(12) United States Patent
Skoda

(10) Patent No.: US 12,744,113 B2
(45) Date of Patent: Sep. 22, 2026

(54) SYSTEMS AND METHODS FOR INTELLIGENT VAPORIZERS

(71) Applicant: Zorday IP, LLC, Mayfield Village, OH (US)

(72) Inventor: Brent M. Skoda, Mayfield Village, OH (US)

(73) Assignee: Zorday IP, LLC

( * ) Notice: Subject to any disclaimer, the term of this patent is extended or adjusted under 35 U.S.C. 154(b) by 0 days.

(21) Appl. No.: 17/744,336

(22) Filed: May 13, 2022

(65) Prior Publication Data

US 2023/0112752 A1 Apr. 13, 2023

Related U.S. Application Data

(63) Continuation of application No. 16/568,020, filed on Sep. 11, 2019, now abandoned, which is a (Continued)

(51) Int. Cl.
*G16H 20/13* (2018.01)
*A24F 40/30* (2020.01)
(Continued)

(52) U.S. Cl.
CPC ............ *G16H 20/13* (2018.01); *A24F 40/30* (2020.01); *A24F 40/42* (2020.01); *A24F 40/65* (2020.01);
(Continued)

(58) Field of Classification Search
CPC .. A61M 11/04; A61M 11/041; A61M 11/042; A61M 11/048; A61M 11/02;
(Continued)

(56) References Cited

U.S. PATENT DOCUMENTS 8,061,149 B1 11/2011 Gowans et al.
8,550,069 B2 10/2013 Alelov
(Continued)

FOREIGN PATENT DOCUMENTS

CN 103960785 A * 8/2014 ............ A24F 40/30
WO WO-2012/006125 A1 1/2012

OTHER PUBLICATIONS

English Machine Translation of CN103960785A provided by Espacenet (Year: 2014).*
(Continued)

*Primary Examiner* — Joseph D. Boecker
*Assistant Examiner* — Brian T Khong
(74) *Attorney, Agent, or Firm* — Foley & Lardner LLP

(57) ABSTRACT

A vaporization and inhalation apparatus comprising a cartridge container configured to receive a cartridge including a liquid. The apparatus includes a heating element configured to heat the liquid to a point of vaporization to generate a vaporized form of the liquid. The apparatus also includes an outlet port through which the vaporized form of the liquid is inhaled. There is also a system for medical dispensing, management and monitoring. According to one aspect, a remote medical management environment can include a medical management system intermediary to a plurality of patients and a plurality of medical care providers. The medical management system can communicate with medical dispensing devices configured to dispense medication to patients. The remote medical management environment can allow medical care providers, such as doctors, the ability to remotely manage and administer medications to patients, while at the same time, avoid accidental medicinal drug use and abuse by patients.

19 Claims, 12 Drawing Sheets

Related U.S. Application Data continuation-in-part of application No. 16/386,600, filed on Apr. 17, 2019, now abandoned, and a continuation-in-part of application No. 16/375,372, filed on Apr. 4, 2019, now abandoned, said application No. 16/386,600 is a continuation of application No. 15/048,575, filed on Feb. 19, 2016, now abandoned, said application No. 16/375,372 is a continuation of application No. 15/047,332, filed on Feb. 18, 2016, now abandoned.

(60) Provisional application No. 62/118,869, filed on Feb. 20, 2015, provisional application No. 62/118,341, filed on Feb. 19, 2015.

(51) Int. Cl.

| | |
|---|---|
| ***A24F 40/42*** | (2020.01) |
| ***A24F 40/65*** | (2020.01) |
| ***G16H 40/63*** | (2018.01) |
| ***H04L 67/02*** | (2022.01) |
| ***H04L 67/025*** | (2022.01) |
| ***H04L 67/10*** | (2022.01) |
| ***H04L 67/1097*** | (2022.01) |
| ***H04L 67/12*** | (2022.01) |
| ***H04L 67/52*** | (2022.01) |
| ***H04L 67/56*** | (2022.01) |

(52) U.S. Cl.

CPC ............. *G16H 40/63* (2018.01); *H04L 67/02* (2013.01); *H04L 67/025* (2013.01); *H04L 67/10* (2013.01); *H04L 67/1097* (2013.01); *H04L 67/52* (2022.05); *H04L 67/56* (2022.05); *H04L 67/12* (2013.01)

(58) Field of Classification Search

CPC .............. A61M 15/00; A61M 15/0001; A61M 15/0003; A61M 15/0021; A61M 15/005; A61M 15/008; A61M 15/06; A61M 15/003; A61M 15/0065; A24F 40/30; A24F 40/00; A24F 40/05; A24F 40/10; A24F 40/20; A24F 40/40; A24F 40/42; A24F 40/44; A24F 40/46; A24F 40/465; A24F 40/48; A24F 40/485; A24F 40/49; A24F 40/50; A24F 40/51; A24F 40/53; A24F 40/57; A24F 40/60; A24F 40/65; A24F 47/002; A24F 47/004; A24F 47/008

See application file for complete search history.

(56) References Cited

U.S. PATENT DOCUMENTS

| | | | | |
|---|---|---|---|---|
| 8,577,734 | B2 | 11/2013 | Treyz et al. | |
| 8,905,964 | B2 | 12/2014 | Poutiatine et al. | |
| 9,747,424 | B2 | 8/2017 | Sablinski | |
| 9,953,140 | B2 | 4/2018 | Mclean et al. | |
| 2005/0072857 | A1 | 4/2005 | Golubev et al. | |
| 2013/0220315 | A1 | 8/2013 | Conley et al. | |
| 2013/0340775 | A1 | 12/2013 | Juster et al. | |
| 2014/0060556 | A1 | 3/2014 | Liu | |
| 2014/0123989 | A1 | 5/2014 | Lamothe | |
| 2014/0174459 | A1 | 6/2014 | Burstyn | |
| 2014/0190496 | A1* | 7/2014 | Wensley | A61M 11/042 131/273 |
| 2014/0246035 | A1 | 9/2014 | Minskoff et al. | |
| 2014/0261488 | A1 | 9/2014 | Tucker | |
| 2015/0038898 | A1 | 2/2015 | Palmer et al. | |
| 2015/0122252 | A1* | 5/2015 | Frija | A24F 40/65 128/202.21 |
| 2015/0136158 | A1* | 5/2015 | Stevens | A61M 11/042 131/329 |
| 2015/0142387 | A1 | 5/2015 | Alarcon et al. | |
| 2015/0174349 | A1 | 6/2015 | Tunnell et al. | |
| 2015/0181945 | A1 | 7/2015 | Tremblay | |
| 2015/0196060 | A1 | 7/2015 | Wensley et al. | |
| 2015/0223521 | A1* | 8/2015 | Menting | A24F 40/50 131/273 |
| 2015/0224268 | A1 | 8/2015 | Henry et al. | |
| 2015/0245654 | A1 | 9/2015 | Memari et al. | |
| 2015/0250961 | A1 | 9/2015 | Whitman et al. | |
| 2015/0327596 | A1* | 11/2015 | Alarcon | H04L 67/535 131/328 |
| 2015/0336689 | A1 | 11/2015 | Brown et al. | |
| 2016/0050974 | A1 | 2/2016 | Galloway et al. | |
| 2016/0089508 | A1* | 3/2016 | Smith | A61M 15/0085 128/202.21 |
| 2016/0090288 | A1 | 3/2016 | Givens et al. | |
| 2016/0095356 | A1 | 4/2016 | Chan | |
| 2016/0106142 | A1 | 4/2016 | Contractor et al. | |
| 2016/0166786 | A1 | 6/2016 | Kinzer | |
| 2016/0211693 | A1 | 7/2016 | Stevens et al. | |
| 2016/0286865 | A1 | 10/2016 | King et al. | |
| 2016/0331026 | A1 | 11/2016 | Cameron | |

OTHER PUBLICATIONS

Final Office Action on U.S. Appl. No. 16/375,372 Dtd Jul. 16, 2021.

Final Office Action on U.S. Appl. No. 16/568,020 Dtd Nov. 15, 2021.

Final Office Action on U.S. Appl. No. 17/721,539 Dtd Feb. 14, 2023.

Final Office Action on U.S. Appl. No. 18/232,999 Dtd Apr. 26, 2024.

Non-Final Office Action on U.S. Appl. No. 15/047,332 Dtd Oct. 5, 2018.

Non-Final Office Action on U.S. Appl. No. 15/048,575 Dtd Oct. 18, 2018.

Non-Final Office Action on U.S. Appl. No. 16/375,372 Dtd Feb. 11, 2022.

Non-Final Office Action on U.S. Appl. No. 16/375,372 Dtd Oct. 2, 2020.

Non-Final Office Action on U.S. Appl. No. 16/386,600 Dtd Oct. 18, 2021.

Non-Final Office Action on U.S. Appl. No. 16/568,001 Dtd Jan. 7, 2021.

Non-Final Office Action on U.S. Appl. No. 16/568,020 Dtd Feb. 2, 2021.

Non-Final Office Action on U.S. Appl. No. 17/751,612 Dtd Jan. 25, 2024.

U.S. Office Action on U.S. Appl. No. 16/568,001 Dtd Aug. 25, 2021.

U.S. Office Action on U.S. Appl. No. 16/574,319 Dtd Dec. 24, 2021.

U.S. Office Action on U.S. Appl. No. 16/574,319 Dtd Apr. 27, 2021.

* cited by examiner

SYSTEMS AND METHODS FOR INTELLIGENT VAPORIZERS

RELATED APPLICATION

This application is a continuation of, and claims priority to and the benefit of U.S. patent application Ser. No. 16/568,020, titled "SYSTEMS AND METHODS FOR INTELLIGENT VAPORIZERS," and filed Sep. 11, 2019, which is a continuation-in-part of, and claims priority to and the benefit of U.S. patent application Ser. No. 16/386,600, titled "SYSTEMS AND METHODS FOR INTELLIGENT VAPORIZERS," and filed Apr. 17, 2019, which claims priority to and the benefit of U.S. patent application Ser. No. 15/048,575, titled "SYSTEMS AND METHODS FOR INTELLIGENT VAPORIZERS," and filed Feb. 19, 2016, which claims priority to and the benefit of U.S. Provisional Patent Application No. 62/118,869, titled "SYSTEMS AND METHODS FOR INTELLIGENT VAPORIZERS," and filed Feb. 20, 2015; U.S. patent application Ser. No. 16/568,020 is also a continuation-in-part of, and claims priority to and the benefit of U.S. patent application Ser. No. 16/375,372, titled "SYSTEMS AND METHODS FOR MEDICAL DISPENSING, MANAGEMENT AND MONITORING," and filed Apr. 4, 2019, which is a continuation of and claims priority to and the benefit of U.S. patent application Ser. No. 15/047,332, titled "SYSTEMS AND METHODS FOR MEDICAL DISPENSING, MANAGEMENT AND MONITORING," and filed Feb. 18, 2016, which claims priority to U.S. Provisional Patent Application No. 62/118,341, titled "SYSTEMS AND METHODS FOR MEDICAL DISPENSING, MANAGEMENT AND MONITORING," and filed Feb. 19, 2015. The contents of all of which are hereby incorporated herein by reference in its entirety for all purposes.

TECHNICAL FIELD

The present application relates generally to apparatuses and systems for operating vaporizers and inhalers. The present application also relates generally to systems and methods for medical dispensing, management and monitoring, and more particularly, to methods and systems for providing medical care providers the ability to remotely manage and monitor the administering of medications to patients via remotely controlled medical dispensing devices.

BACKGROUND

Vaporizers or inhalers may be used to administer, transform or otherwise dispense a substance in a consumable format (i.e. vapor, fine powder, mist, liquid) for the user. One form of vaporizers includes electronic cigarettes. The substance for consumption through a vaporizer or vaporization apparatus or device may include Caffeine, an energy boosting formulation, a flavored substance, a medicinal formula, a supplement, a vitamin, a mineral, any ingredient officially monographed and listed in the Homeopathic Pharmacopeia of the United States of America (the "HPUS"), or various other products for consumption alone or in combination. Vaporizers configured for consumption by a user via inhaling may be operated through the use of various electronic components configured to heat the substance, which substance may be stored as a liquid, to transform the liquid substance into a vapor phase and present the substance for consumption to the user via an outlet port configured to permit inhaling of the substance. Furthermore, patients in need of medication either have to visit pharmacies to pick up medication or have the medicines delivered to them. Oftentimes, doctors treating these patients are unable to gauge the efficacy of the medications they prescribe until the patient either returns to the clinic for follow up testing or goes to a laboratory for blood work.

SUMMARY OF THE INVENTION

Various embodiments disclosed herein provide apparatuses, systems, and methods related to the operation of a device configured to convert substances into a form configured for consumption by inhalation.

Various embodiments provide a vaporization and inhalation apparatus or device configured to vaporize a substance such as liquid contained in a cartridge through heating of the liquid to a point of vaporization. The device is further configured to permit a user to consume the vapor through inhaling via an outlet port in the device. In particular embodiments, the vaporization device includes at least one sensor device configured to determine a quantity of consumption from the cartridge based on the vapor draw. The device may include a counter and/or a timer configured to determine the number of vapor draws and or the duration of a vapor draw. The timer may be configured to determine the length of a vapor draw, for example based on a change in pressure in the device during consumption by the user. The timer may be configured to additionally or alternatively determine the duration of a heating event associated with the electronic heating or other heating of the substance to form a vapor in connection with a vapor draw request by a user. The device further includes at least one specially programmed processor configured to, based on the duration of the vapor draw and/or heating event associated with the vapor draw, determine a value associated with an estimate of a quantity consumed. The vapor draw may be based on predetermined aerosol tests. In particular embodiments, the specially programmed processor may determine power consumption to determine the duration of a vapor draw and/or a heating even to determine a value associated with an estimate of quantity consumed. The specially programmed processor may be configured to vary the consumption rate based on the sensed or measured power or time based on the substance in the cartridge. For example, the cartridge may include a unique identification code associated with particular substances. The processor may be calibrated such that the processor is configured to associate a particular consumption rate with particular substances to account for variations in heating rates for different substances. In various embodiments, the cartridge may be programmable and/or may include one or more memory device that may be communicably coupled with a processor in the vaporization device to provide identifying information such as substance contained therein and to provide historical information such number of prior uses, if any, remaining quantity on-board or initial quantity on-board, etc.

In various embodiments, the processor of the vaporization device may be configured to cause various actions based on the consumption determination. For example, the processor may be configured to prompt a refill request based on the quantity in the cartridge falling below a certain threshold, to replenish a supply to a user on time. The threshold may be pre-programmed, user specified, and/or may be automatically or manually adjustable based on user habits, locations, estimated time of delivery, or other aspects that may be programmed or learned through storage of various behavior aspects. In various embodiments, the vaporization device may include a location based system and/or may include a wireless transmitter configured to connect the device to one or more networks, such as the Internet. Accordingly, the vaporization device may, in response to prompting a refill request, determine the best mode of refilling and may transmit the request to a local distributer, including, but not limited to a pharmacy. The refill request may indicate a user's location, cartridge substance identifying information. The request may facilitate a refill cartridge be sent directly to the user at a pre-set location. The refill request may automatically send the refill to the closest distributor and/or may send the refill directly to the user. The vaporization device may store the quantity of refills consumed in the device, the date, or rate of refill requests for a user, the rate of consumption, the location of consumption, the time of consumption, dosage requirements, substance flavor when applicable, the substance consumed, and any other relevant information pertaining to the substance the user, the substance, or any relevant third party (i.e. doctor, pharmacist, manufacturer, distributor, storage temperatures, that would be relevant and known to one skilled in the art of whatever substance is being dispensed). Any of the aforementioned parameters may be stored separately or may be aggregated, for example to create a user profile and to enable machine learner and user preferences. The information may be used for advertising purposes and/or to offer discounts, deals on consumable products, or may be implemented in a social networking platform, for example to notify a consumer of others consuming similar substances at nearby locations for social consumption.

Various embodiments provide a vaporization device configured to vaporize a plurality of substances independently or collectively as selected. The plurality of substance includes a plurality of independently stored liquids, for example, contained in a single multi-content cartridge. The vaporization device may be configured to heat one or more of the liquids independently and to vary which one or more of the liquids is heated at any time to allow a user to switch substances for vaporization and or combine different vapors. The vaporization device may be specially programmed to heat different substances for different duration based on the substance. At least one of the device and or the multi-substance cartridge may be configured to identify or determine the substances provided in the cartridge and to permit a user selection of the substances for consumption through inhaling via an outlet port in the device.

Particular embodiments of the multi-substance cartridges may be configured to determine vapor draw quantities and user consumption for one or more of the substances contained in each section of the cartridge in accordance with various other embodiments described herein.

The inventors have appreciated that described embodiments disclosed herein provide vaporization and inhaler apparatuses that permit rapid and automated seamless refilling systems and multi-substance consumption in a compact and behavior assisted machine learning format.

In some implementations, the present disclosure relates to systems and methods for medical dispensing, management and monitoring. According to one aspect, a remote medical management environment can include a medical management system intermediary to a plurality of patients and a plurality of medical care providers. The medical management system can communicate with medical dispensing devices configured to dispense medication to patients. Further, the medical management system can communicate with provider devices through which medical care providers can access medicine related information of patients and provide instructions, which can administer treatment protocols to patients of the medical dispensing devices. The remote medical management environment can allow medical care providers, such as doctors, the ability to remotely manage and administer medications to patients, while at the same time, avoid medicinal drug abuse by patients.

The medical management system can include a processor and a memory including instructions configured to cause the medical management system to allow a medical care provider to remotely manage and administer medications to one or more patients. The medical management system includes a patient database, a provider database, a medical manager and a prescription manager. The medical management system can include one or more communication modules through which the medical management system can communicate with patient devices and provider devices.

The patient device, otherwise referred to as a medical dispensing device can be configured to allow a medical care provider, for example, a doctor, the ability to remotely monitor, regulate and manipulate medication administration to a patient associated with the patient device. Through the medical dispensing device, the medical care provider can adjust either the dosage of medications or the time at which the medication is administered. In some implementations, the medical care provider may receive feedback through the medical dispensing device or other medical device monitoring the patient and adjust the dosage or time at which to administer medication based on the received feedback. The medical dispensing device can be equipped with a communications module that is configured to communicate with the medical management system through which the medical care provider can remotely communicate with the medical dispensing device. The communications module can include both hardware and software components that allow the medical dispensing device to receive and transmit instructions and information. In some implementations, the communications module can be configured to provide wireless communications, for example, BLUETOOTH, WiFi, cellular communications, among others. In some implementations, the communications module can be configured to communicate with another device, such as a smartphone, tablet, or other device that allows the medical dispensing device to receive and execute instructions received from the medical care provider. The medical dispensing device can include one or more electronic actuators that can be configured or programmed to control the amount of medication dispensed from the medical dispensing device.

In some implementations, the medical dispensing device is programmable and capable of maintaining activity logs. The activity logs can identify a date and time at which medication was dispensed, a dosage of medication dispensed as well as any other physiological measurements, for example, temperature, pulse, heart rate, blood pressure, sugar levels, among others, taken around the time the medication was dispensed. In addition to medication dispensing related activity, the activity logs can identify when a medical care provider communicated with the medical dispensing device. In some implementations, the activity logs can include information related to dosage changes as well as changes in the time at which medication is to be administered.

The medical dispensing device can also include sensors measuring a quantity of medication remaining in the medical dispensing device. In some implementations, the medical dispensing device an determine an amount of medication remaining in the medical dispensing device based on the amount of medication included in a medicine cartridge and an amount of medication already dispensed since the medicine cartridge was first inserted. The medical dispensing device can be configured to communicate medicine quantity levels such that refills can be ordered before the medicine cartridge is completely empty.

The medical dispensing device can be tamper proof. This is to prevent medication abuse and fraud. In some implementations, the medical dispensing device can include an alert system that triggers an alert upon determining that the medical dispensing device has been tampered or an attempt to tamper the medical dispensing device was made. In some implementations, the medical dispensing device can include one or more security modules. The security modules can include hardware and software to ensure that the medication is dispensed to an authorized user or patient. In some implementations, the medical dispensing device can include a user recognition or identification system. In some implementations, the medical dispensing device can include a fingerprint reader, an iris scanner, or any other biometric scanner to confirm the identity of the user. In some implementations, the medical dispensing device can be password protected. In some implementations the medical dispensing device can only be actuated via a second device, such as a smartphone or tablet, registered with the medical management system.

In some implementations, the medical dispensing device can include a temperature control module to control the temperature of medication within the medical dispensing device. In this way, if the medicine in the medical dispensing device is to be maintained at a particular temperature, and the medical dispensing device is in a location that has an ambient temperature much higher than the temperature at which to maintain the medicine, the medical dispensing device can provide cooling to the medication. Conversely, the medical dispensing device can provide heating to medications that are supposed to be stored or maintained at temperatures higher than the ambient temperature at which the medical dispensing device is located.

In some implementations, the medical dispensing device can be a programmable, remotely controlled prescription drug bottle. The medical dispensing device may include Bluetooth, RFID, GPS, a battery, a controller, a cellular chip, etc. The medical dispensing device could dispense pills, liquid, powder, any vaporizable substance, collectively, respectively, and independently. The medical dispensing device can be configured to provide the ability to remotely regulate, monitor, control and/or verify dosage. In this way, a medical care provider can regulate or control the number of pills dispensed, the time at which they are dispensed and the location at which they can be dispensed, among others. For instance, if the pills can only be dispensed within a particular geographic location identifiable via cellular triangulation techniques, IP addressing, or GPS coordinates, the risk of drug abuse, theft, resale, and redistribution can be minimized. In some implementations, the medical dispensing device can be configured to only dispense medications when it is within a few feet from a stationary object, such as a RFID scanner or Bluetooth source that may be tied to a particular location.

In some implementations, the medical dispensing device may be configured to communicate with a mobile device of the patient to verify the identity of a person accessing or requesting access to the medical dispensing device. For instance, the medical dispensing device may only dispense medication in response to receiving a communication or signal from a paired mobile device that can generate the communication or signal upon verifying the identity of the patient. In some implementations, the mobile device can verify the identity of the patient through facial recognition, fingerprint scanning, passwords, or other security measures that can be received, identified or otherwise incorporated via the mobile device. In this way, there is no need for the medical dispensing device to be designed with an integrated fingerprint scanner, camera to detect facial recognition, or keypad to receive a password from the patient, thereby reducing manufacturing costs of the medical dispensing device.

In some implementations, the location of the medical dispensing device or the mobile device with which the medical dispensing device can communicate may be monitored. In some implementations, the medical dispensing device can restrict the dispensing of medications based on one or more predetermined locations. In some implementations, one or more location based policies can be established to ensure additional security. For instance, the medical dispensing device may be configured to only dispense the medicine at predetermined locations, for example, a patient's home, a patient's work location, a nursing home, a hospital or other medical care provider's address, among others. In this way, if the device is stolen or otherwise provided to an unauthorized user, the unauthorized user may be unable to receive medication from the medical dispensing device at locations different from the predetermined locations. In addition, the medical dispensing device may only transmit or receive data from the medical management system at the predetermined locations to reduce security breaches.

In some implementations, the medical dispensing device can operate using batteries. In some implementations, the batteries may be rechargeable or disposable. In some implementations in which the batteries are rechargeable, the batteries may be charged via a USB cable, via a power supply channel, or via wireless induction. In some implementations, to implement wireless induction, the medical dispensing device can be incorporated with a wireless charging coil, for example, a wireless charging coil supplied by DIGIKEY and manufactured by Wurth Electronics, Inc. In some implementations, the wireless charging coil can be Part Number 76030811, manufactured by Wurth Electronics, Inc. The shape, size and position of the one or more wireless charging coils can be designed to fit within the medical dispensing device.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The skilled artisan will understand that the drawings primarily are for illustrative purposes and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

The features and advantages of the inventive concepts disclosed herein will become more apparent from the detailed description set forth below when taken in conjunction with the drawings.

DETAILED DESCRIPTION

Following below are more detailed descriptions of various concepts related to, and embodiments of, inventive variable counterweight systems and methods of operating variable counterweight systems. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Section A describes a network environment and computing environment which may be useful for practicing various computing related embodiments described herein.

Section B describes embodiments of systems and methods facilitating consumption of a substance through a vaporization and inhaler apparatus.

Section C describes embodiments of systems and methods for medical dispensing, management and monitoring.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

A. Computing and Network Environment

Figure 1A:
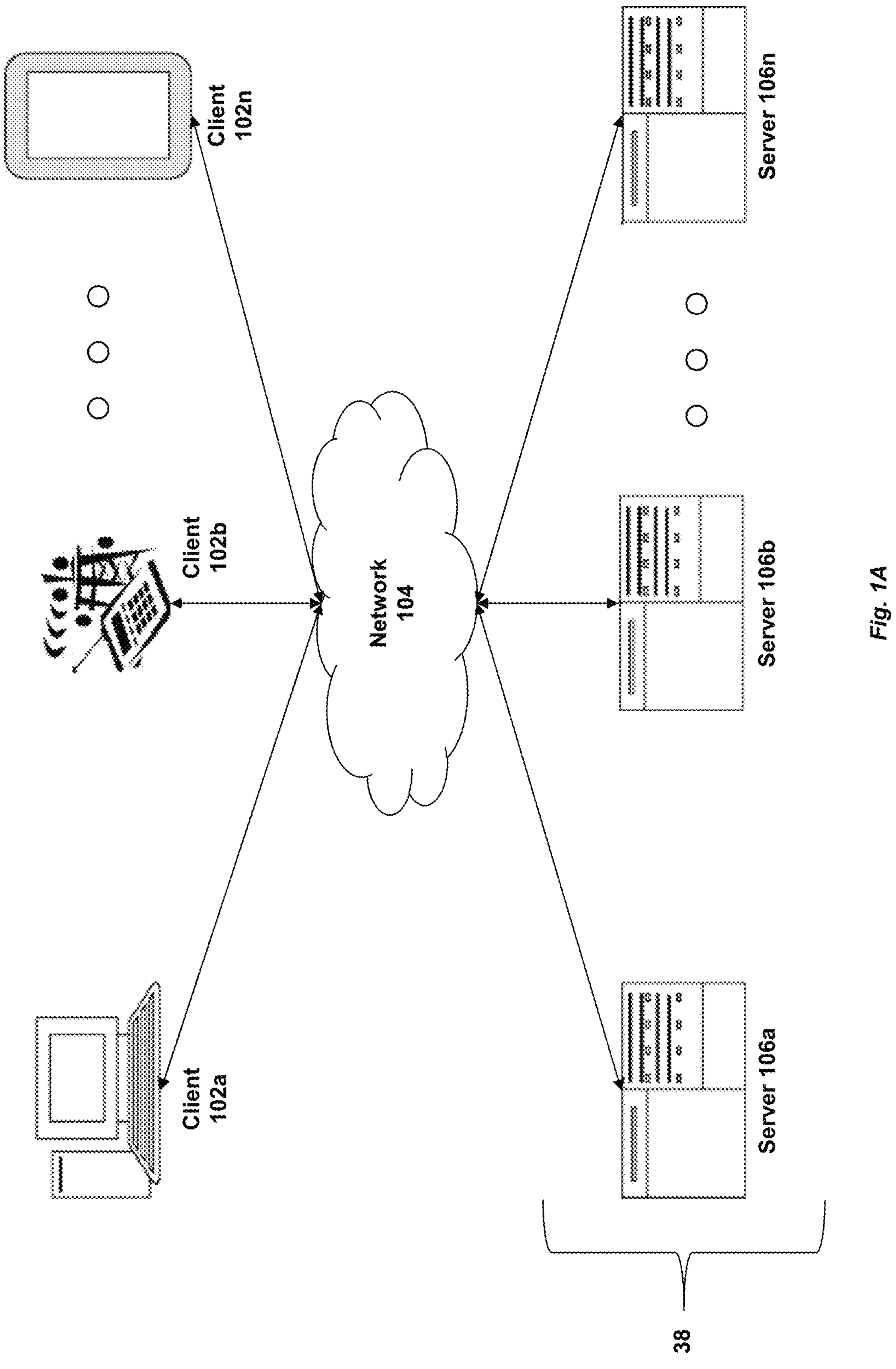
FIG. 1A is a block diagram depicting an embodiment of a network environment comprising client devices in communication with server devices.

Prior to discussing specific inventive embodiments, it may be helpful to describe aspects of the operating environment as well as associated system components (e.g., hardware elements) in connection with the methods and systems described herein. Referring to FIG. 1A, an embodiment of a network environment is depicted. In brief overview, the illustrated exploring network environment includes one or more clients 102a-102n (also generally referred to as local machine(s) 102, client(s) 102, client node(s) 102, client machine(s) 102, client computer(s) 102, client device(s) 102, endpoint(s) 102, or endpoint node(s) 102) in communication with one or more servers 106a-106n (also generally referred to as server(s) 106, node 106, or remote machine(s) 106) via one or more networks 104. In some embodiments, a client 102 has the capacity to function as both a client node seeking access to resources provided by a server and as a server providing access to hosted resources for other clients 102a-102n.

Although FIG. 1A shows a network 104 between the clients 102 and the servers 106, the clients 102 and the servers 106 may be on the same network 104. In some embodiments, there are multiple networks 104 between the clients 102 and the servers 106. In one of these embodiments, a network 104' (not shown) may be a private network and a network 104 may be a public network. In another of these embodiments, a network 104 may be a private network and a network 104' a public network. In still another of these embodiments, networks 104 and 104' may both be private networks.

The network 104 may be connected via wired or wireless links. Wired links may include Digital Subscriber Line (DSL), coaxial cable lines, or optical fiber lines. The wireless links may include BLUETOOTH, Wi-Fi, NFC, RFID Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 4G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

The network 104 may be any type and/or form of network. The geographical scope of the network 104 may vary widely and the network 104 can be a body area network (BAN), a personal area network (PAN), a local-area network (LAN), e.g. Intranet, a metropolitan area network (MAN), a wide area network (WAN), or the Internet. The topology of the network 104 may be of any form and may include, e.g., any of the following: point-to-point, bus, star, ring, mesh, or tree. The network 104 may be an overlay network, which is virtual and sits on top of one or more layers of other networks 104'. The network 104 may be of any such network topology as known to those ordinarily skilled in the art capable of supporting the operations described herein. The network 104 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 104 may be a type of a broadcast network, a telecommunications network, a data communication network, or a computer network.

In some embodiments, the system may include multiple, logically-grouped servers 106. In one of these embodiments, the logical group of servers may be referred to as a server farm 38 or a machine farm 38. In another of these embodiments, the servers 106 may be geographically dispersed. In other embodiments, a machine farm 38 may be administered as a single entity. In still other embodiments, the machine farm 38 includes a plurality of machine farms 38. The servers 106 within each machine farm 38 can be heterogeneous—one or more of the servers 106 or machines 106 can operate according to one type of operating system platform (e.g., WINDOWS NT, manufactured by Microsoft Corp. of Redmond, Washington), while one or more of the other servers 106 can operate on according to another type of operating system platform (e.g., Unix, Linux, or Mac OS X).

In one embodiment, servers 106 in the machine farm 38 may be stored in high-density rack systems, along with associated storage systems, and located in an enterprise data center. In this embodiment, consolidating the servers 106 in this way may improve system manageability, data security, the physical security of the system, and system performance by locating servers 106 and high performance storage systems on localized high performance networks. Centralizing the servers 106 and storage systems and coupling them with advanced system management tools allows more efficient use of server resources.

The servers 106 of each machine farm 38 do not need to be physically proximate to another server 106 in the same machine farm 38. Thus, the group of servers 106 logically grouped as a machine farm 38 may be interconnected using a wide-area network (WAN) connection or a metropolitan-area network (MAN) connection. For example, a machine farm 38 may include servers 106 physically located in different continents or different regions of a continent, country, state, city, campus, or room. Data transmission speeds between servers 106 in the machine farm 38 can be increased if the servers 106 are connected using a local-area network (LAN) connection or some form of direct connection. Additionally, a heterogeneous machine farm 38 may include one or more servers 106 operating according to a type of operating system, while one or more other servers 106 execute one or more types of hypervisors rather than operating systems. In these embodiments, hypervisors may be used to emulate virtual hardware, partition physical hardware, virtualized physical hardware, and execute virtual machines that provide access to computing environments, allowing multiple operating systems to run concurrently on a host computer. Native hypervisors may run directly on the host computer. Hypervisors may include VMware ESX/ESXi, manufactured by VMWare, Inc., of Palo Alto, California; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTUALBOX.

Management of the machine farm 38 may be de-centralized. For example, one or more servers 106 may comprise components, subsystems and modules to support one or more management services for the machine farm 38. In one of these embodiments, one or more servers 106 provide functionality for management of dynamic data, including techniques for handling failover, data replication, and increasing the robustness of the machine farm 38. Each server 106 may communicate with a persistent store and, in some embodiments, with a dynamic store.

Server 106 may be a file server, application server, web server, proxy server, appliance, network appliance, gateway, gateway server, virtualization server, deployment server, SSL VPN server, or firewall. In one embodiment, the server 106 may be referred to as a remote machine or a node. In another embodiment, a plurality of nodes 290 may be in the path between any two communicating servers.

Figure 1B:
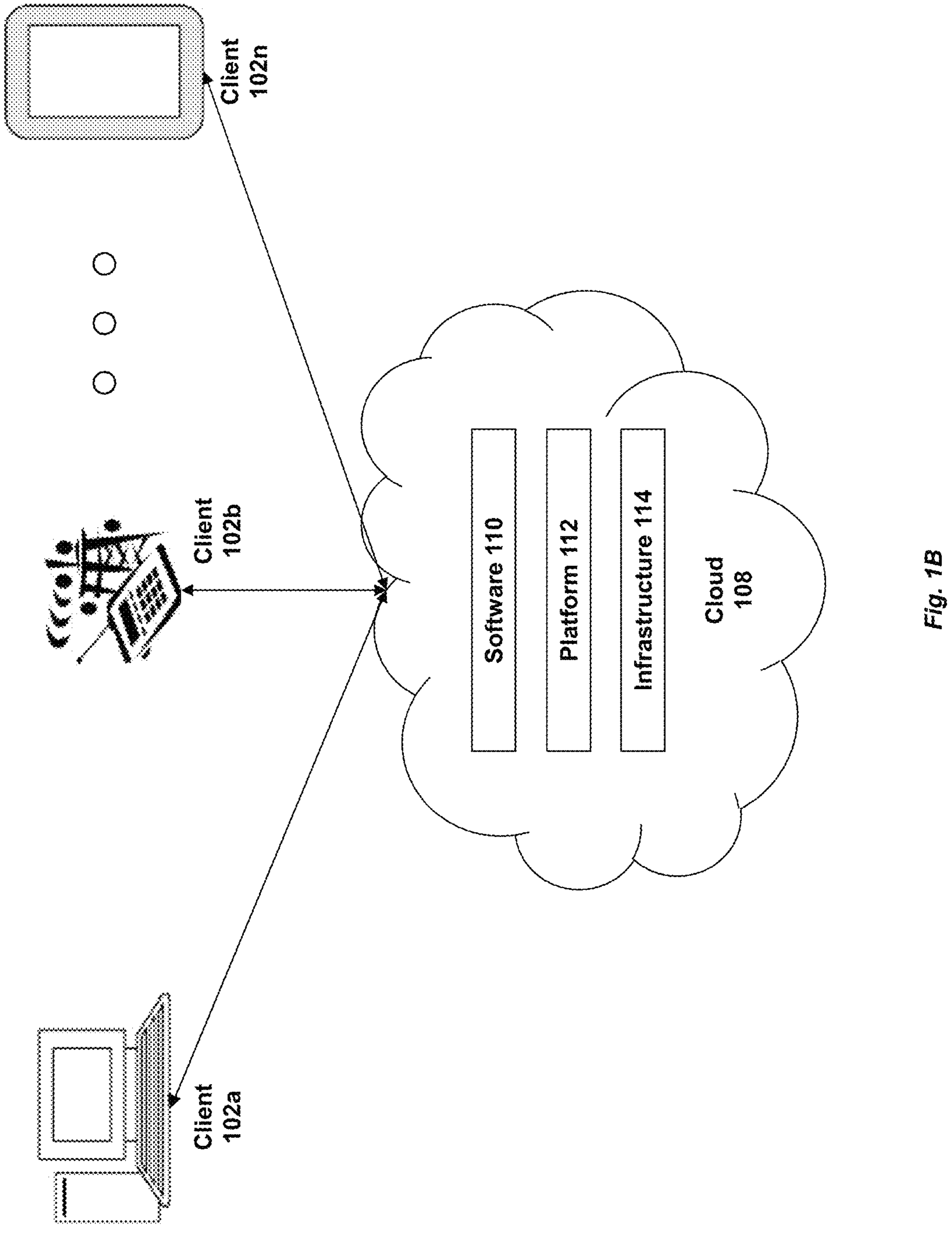
FIG. 1B is a block diagram depicting a cloud computing environment comprising client devices in communication with a cloud service provider.

Referring to FIG. 1B, a cloud computing environment is depicted. A cloud computing environment may provide client 102 with one or more resources provided by a network environment. The cloud computing environment may include one or more clients 102*a*-102*n*, in communication with the cloud 108 over one or more networks 104. Clients 102 may include, e.g., thick clients, thin clients, and zero clients. A thick client may provide at least some functionality even when disconnected from the cloud 108 or servers 106. A thin client or a zero client may depend on the connection to the cloud 108 or server 106 to provide functionality. A zero client may depend on the cloud 108 or other networks 104 or servers 106 to retrieve operating system data for the client device. The cloud 108 may include back end platforms, e.g., servers 106, storage, server farms or data centers.

The cloud 108 may be public, private, or hybrid. Public clouds may include public servers 106 that are maintained by third parties to the clients 102 or the owners of the clients. The servers 106 may be located off-site in remote geographical locations as disclosed above or otherwise. Public clouds may be connected to the servers 106 over a public network. Private clouds may include private servers 106 that are physically maintained by clients 102 or owners of clients. Private clouds may be connected to the servers 106 over a private network 104. Hybrid clouds 108 may include both the private and public networks 104 and servers 106.

The cloud 108 may also include a cloud based delivery, e.g. Software as a Service (SaaS) 110, Platform as a Service (PaaS) 112, and Infrastructure as a Service (IaaS) 114. IaaS may refer to a user renting the use of infrastructure resources that are needed during a specified time period. IaaS providers may offer storage, networking, servers or virtualization resources from large pools, allowing the users to quickly scale up by accessing more resources as needed. Examples of IaaS include AMAZON WEB SERVICES provided by Amazon.com, Inc., of Seattle, Washington, RACKSPACE CLOUD provided by Rackspace US, Inc., of San Antonio, Texas, Google Compute Engine provided by Google Inc. of Mountain View, California, or RIGHTSCALE provided by RightScale, Inc., of Santa Barbara, California. PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Washington, Google App Engine provided by Google Inc., and HEROKU provided by Heroku, Inc. of San Francisco, California. SaaS providers may offer the resources that PaaS provides, including storage, networking, servers, virtualization, operating system, middleware, or runtime resources. In some embodiments, SaaS providers may offer additional resources including, e.g., data and application resources. Examples of SaaS include GOOGLE APPS provided by Google Inc., SALESFORCE provided by Salesforce.com Inc. of San Francisco, California, or OFFICE 365 provided by Microsoft Corporation. Examples of SaaS may also include data storage providers, e.g. DROPBOX provided by Dropbox, Inc. of San Francisco, California, Microsoft SKYDRIVE provided by Microsoft Corporation, Google Drive provided by Google Inc., or Apple ICLOUD provided by Apple Inc. of Cupertino, California.

Clients 102 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 102 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 102 may access SaaS resources through the use of web-based user interfaces, provided by a web browser (e.g. GOOGLE CHROME, Microsoft INTERNET EXPLORER, or Mozilla Firefox provided by Mozilla Foundation of Mountain View, California). Clients 102 may also access SaaS resources through smartphone or tablet applications, including, e.g., Salesforce Sales Cloud, or Google Drive app. Clients 102 may also access SaaS resources through the client operating system, including, e.g., Windows file system for DROPBOX.

In some embodiments, access to IaaS, PaaS, or SaaS resources may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

Figure 1C:
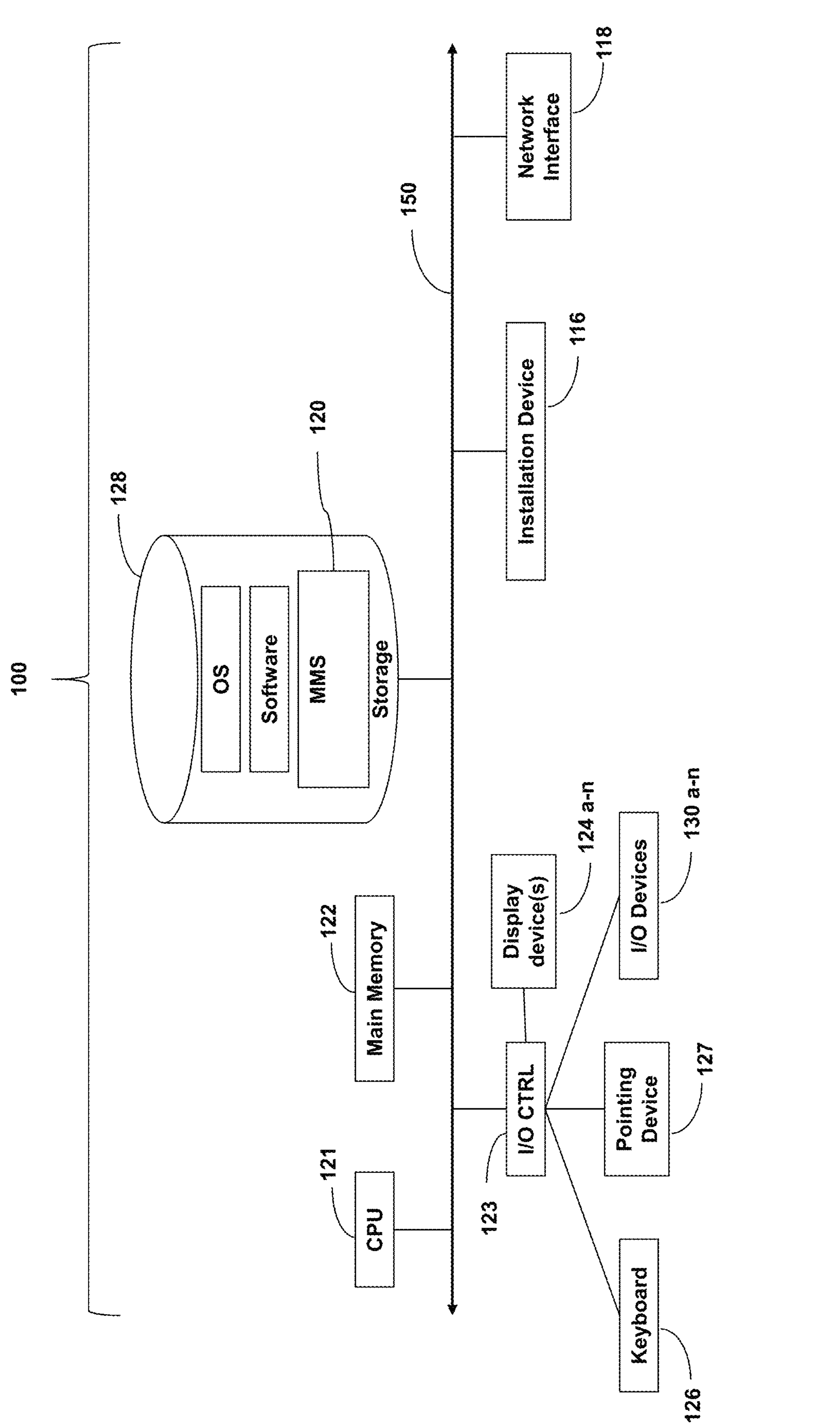
FIGS. 1C and 1D are block diagrams depicting embodiments of computing devices useful in connection with the methods and systems described herein.
Figure 1D:
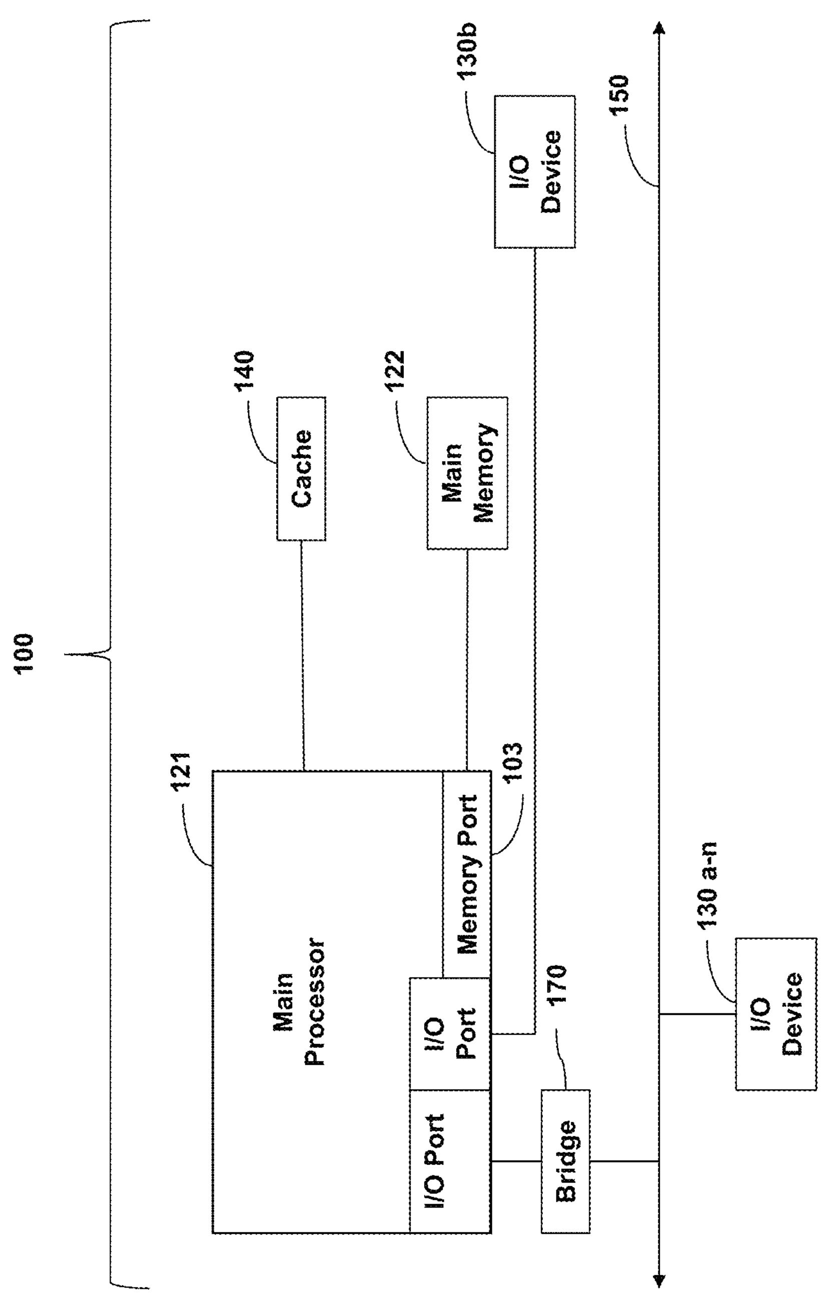

The client 102 and server 106 may be deployed as and/or executed on any type and form of computing device, e.g. a computer, network device or appliance capable of communicating on any type and form of network and performing the operations described herein. FIGS. 1C and 1D depict block diagrams of a computing device 100 useful for practicing an embodiment of the client 102 or a server 106. As shown in FIGS. 1C and 1D, each computing device 100 includes a central processing unit 121, and a main memory unit 122. As shown in FIG. 1C, a computing device 100 may include a storage device 128, an installation device 116, a network interface 118, an I/O controller 123, display devices 124*a*-124*n*, a keyboard 126 and a pointing device 127, e.g. a mouse. The storage device 128 may include, without limitation, an operating system, software, and a software of a medical management system (MMS) 120. As shown in FIG. 1D, each computing device 100 may also include additional optional elements, e.g. a memory port 103, a bridge 170, one or more input/output devices 130*a*-130*n* (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit, e.g.: those manufactured by Intel Corporation of Mountain View, California; those manufactured by Motorola Corporation of Schaumburg, Illinois; the ARM processor and TEGRA system on a chip (SoC) manufactured by Nvidia of Santa Clara, California; the POWER7 processor, those manufactured by International Business Machines of White Plains, New York; or those manufactured by Advanced Micro Devices of Sunnyvale, California. The computing device 100 may be based on any of these processors, or any other processor capable of operating as described herein. The central processing unit 121 may utilize instruction level parallelism, thread level parallelism, different levels of cache, and multi-core processors. A multi-core processor may include two or more processing units on a single computing component. Examples of multi-core processors include the AMD PHENOM IIX2, INTEL CORE i5 and INTEL CORE i7.

Main memory unit 122 may include one or more memory chips capable of storing data and allowing any storage location to be directly accessed by the microprocessor 121. Main memory unit 122 may be volatile and faster than storage 128 memory. Main memory units 122 may be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 122 or the storage 128 may be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 122 may be based on any of the above described memory chips, or any other available memory chips capable of operating as described herein. In the embodiment shown in FIG. 1C, the processor 121 communicates with main memory 122 via a system bus 150 (described in more detail below). FIG. 1D depicts an embodiment of a computing device 100 in which the processor communicates directly with main memory 122 via a memory port 103. For example, in FIG. 1D the main memory 122 may be DRDRAM.

FIG. 1D depicts an embodiment in which the main processor 121 communicates directly with cache memory 140 via a secondary bus, sometimes referred to as a backside bus. In other embodiments, the main processor 121 communicates with cache memory 140 using the system bus 150. Cache memory 140 typically has a faster response time than main memory 122 and is typically provided by SRAM, BSRAM, or EDRAM. In the embodiment shown in FIG. 1D, the processor 121 communicates with various I/O devices 130 via a local system bus 150. Various buses may be used to connect the central processing unit 121 to any of the I/O devices 130, including a PCI bus, a PCI-X bus, or a PCI-Express bus, or a NuBus. For embodiments in which the I/O device is a video display 124, the processor 121 may use an Advanced Graphics Port (AGP) to communicate with the display 124 or the I/O controller 123 for the display 124. FIG. 1D depicts an embodiment of a computer 100 in which the main processor 121 communicates directly with I/O device 130*b* or other processors 121' via HYPERTRANS- PORT, RAPIDIO, or INFINIBAND communications technology. FIG. 1D also depicts an embodiment in which local busses and direct communication are mixed: the processor 121 communicates with I/O device 130*a* using a local interconnect bus while communicating with I/O device 130*b* directly.

A wide variety of I/O devices 130*a*-130*n* may be present in the computing device 100. Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjetprinters, laser printers, and 3D printers.

Devices 130*a*-130*n* may include a combination of multiple input or output devices, including, e.g., Microsoft KINECT, Nintendo Wiimote for the WII, Nintendo WII U GAMEPAD, or Apple IPHONE. Some devices 130*a*-130*n* allow gesture recognition inputs through combining some of the inputs and outputs. Some devices 130*a*-130*n* provides for facial recognition which may be utilized as an input for different purposes including authentication and other commands. Some devices 130*a*-130*n* provides for voice recognition and inputs, including, e.g., Microsoft KINECT, SIRI for IPHONE by Apple, Google Now or Google Voice Search.

Additional devices 130*a*-130*n* have both input and output capabilities, including, e.g., haptic feedback devices, touchscreen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touchscreen devices, including, e.g., Microsoft PIXELSENSE or Multi-Touch Collaboration Wall, may have larger surfaces, such as on a table-top or on a wall, and may also interact with other electronic devices. Some I/O devices 130*a*-130*n*, display devices 124*a*-124*n* or group of devices may be augment reality devices. The I/O devices may be controlled by an I/O controller 123 as shown in FIG. 1C. The I/O controller may control one or more I/O devices, such as, e.g., a keyboard 126 and a pointing device 127, e.g., a mouse or optical pen. Furthermore, an I/O device may also provide storage and/or an installation medium 116 for the computing device 100. In still other embodiments, the computing device 100 may provide USB connections (not shown) to receive handheld USB storage devices. In further embodiments, an I/O device 130 may be a bridge between the system bus 150 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 124*a*-124*n* may be connected to I/O controller 123. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g. stereoscopy, polarization filters, active shutters, or autostereoscopy. Display devices 124*a*-124*n* may also be a head-mounted display (HMD). In some embodiments, display devices 124*a*-124*n* or the corresponding I/O controllers 123 may be controlled through or have hardware support for OPENGL or DIRECTX API or other graphics libraries.

In some embodiments, the computing device 100 may include or connect to multiple display devices 124*a*-124*n*, which each may be of the same or different type and/or form. As such, any of the I/O devices 130*a*-130*n* and/or the I/O controller 123 may include any type and/or form of suitable hardware, software, or combination of hardware and software to support, enable or provide for the connection and use of multiple display devices 124*a*-124*n* by the computing device 100. For example, the computing device 100 may include any type and/or form of video adapter, video card, driver, and/or library to interface, communicate, connect or otherwise use the display devices 124*a*-124*n*. In one embodiment, a video adapter may include multiple connectors to interface to multiple display devices 124*a*-124*n*. In other embodiments, the computing device 100 may include multiple video adapters, with each video adapter connected to one or more of the display devices 124*a*-124*n*. In some embodiments, any portion of the operating system of the computing device 100 may be configured for using multiple displays 124*a*-124*n*. In other embodiments, one or more of the display devices 124*a*-124*n* may be provided by one or more other computing devices 100*a* or 100*b* connected to the computing device 100, via the network 104. In some embodiments software may be designed and constructed to use another computer's display device as a second display device 124*a* for the computing device 100. For example, in one embodiment, an Apple iPad may connect to a computing device 100 and use the display of the device 100 as an additional display screen that may be used as an extended desktop. One ordinarily skilled in the art will recognize and appreciate the various ways and embodiments that a computing device 100 may be configured to have multiple display devices 124*a*-124*n*.

Referring again to FIG. 1C, the computing device 100 may comprise a storage device 128 (e.g. one or more hard disk drives or redundant arrays of independent disks) for storing an operating system or other related software, and for storing application software programs such as any program related to the software for the medical management system 120. Examples of storage device 128 include, e.g., hard disk drive (HDD); optical drive including CD drive, DVD drive, or BLU-RAY drive; solid-state drive (SSD); USB flash drive; or any other device suitable for storing data. Some storage devices may include multiple volatile and non-volatile memories, including, e.g., solid state hybrid drives that combine hard disks with solid state cache. Some storage device 128 may be non-volatile, mutable, or read-only. Some storage device 128 may be internal and connect to the computing device 100 via a bus 150. Some storage device 128 may be external and connect to the computing device 100 via an I/O device 130 that provides an external bus. Some storage device 128 may connect to the computing device 100 via the network interface 118 over a network 104, including, e.g., the Remote Disk for MACBOOK AIR by Apple. Some client devices 100 may not require a non-volatile storage device 128 and may be thin clients or zero clients 102. Some storage device 128 may also be used as an installation device 116, and may be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Client device 100 may also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. An application distribution platform may facilitate installation of software on a client device 102. An application distribution platform may include a repository of applications on a server 106 or a cloud 108, which the clients **102*a*-102*n* may access over a network 104. An application distribution platform may include application developed and provided by various developers. A user of a client device 102** may select, purchase and/or download an application via the application distribution platform.

Furthermore, the computing device 100 may include a network interface 118 to interface to the network 104 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 100 communicates with other computing devices 100' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Florida. The network interface 118 may comprise a built-in network adapter, network interface card, PCMCIA network card, EXPRESSCARD network card, card bus network adapter, wireless network adapter, USB network adapter, modem or any other device suitable for interfacing the computing device 100 to any type of network capable of communication and performing the operations described herein.

A computing device 100 of the sort depicted in FIGS. 1B and 1C may operate under the control of an operating system, which controls scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Washington; MAC OS and iOS, manufactured by Apple, Inc. of Cupertino, California; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, California, among others. Some operating systems, including, e.g., the CHROME OS by Google, may be used on zero clients or thin clients, including, e.g., CHROMEBOOKS.

The computer system 100 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 100 has sufficient processor power and memory capacity to perform the operations described herein.

In some embodiments, the computing device 100 may have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 100 is a gaming system. For example, the computer system 100 may comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, an XBOX 360 device manufactured by the Microsoft Corporation of Redmond, Washington.

In some embodiments, the computing device 100 is a digital audio player such as the Apple IPOD, IPOD Touch, and IPOD NANO lines of devices, manufactured by Apple Computer of Cupertino, California. Some digital audio players may have other functionality, including, e.g., a gaming system or any functionality made available by an application from a digital application distribution platform. For example, the IPOD Touch may access the Apple App Store. In some embodiments, the computing device 100 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 100 is a tablet e.g. the IPAD line of devices by Apple; GALAXY TAB family of devices by Samsung; or KINDLE FIRE, by Amazon.com, Inc. of Seattle, Washington. In other embodiments, the computing device 100 is an eBook reader, e.g. the KINDLE family of devices by Amazon.com, or NOOK family of devices by Barnes & Noble, Inc. of New York City, New York.

In some embodiments, the communications device 102 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc; or a Motorola DROID family of smartphones. In yet another embodiment, the communications device 102 is a laptop or desktop computer equipped with a web browser and a microphone and speaker system, e.g. a telephony headset. In these embodiments, the communications devices 102 are web-enabled and can receive and initiate phone calls. In some embodiments, a laptop or desktop computer is also equipped with a webcam or other video capture device that enables video chat and video call. In some embodiments, the communication device 102 is a wearable mobile computing device including but not limited to Google Glass and Samsung Gear.

In some embodiments, the status of one or more machines 102, 106 in the network 104 is monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the vaporization apparatus and related systems and methods disclosed herein.

B. Systems and Methods of a Vaporization and Inhaler Apparatus

Figure 2:
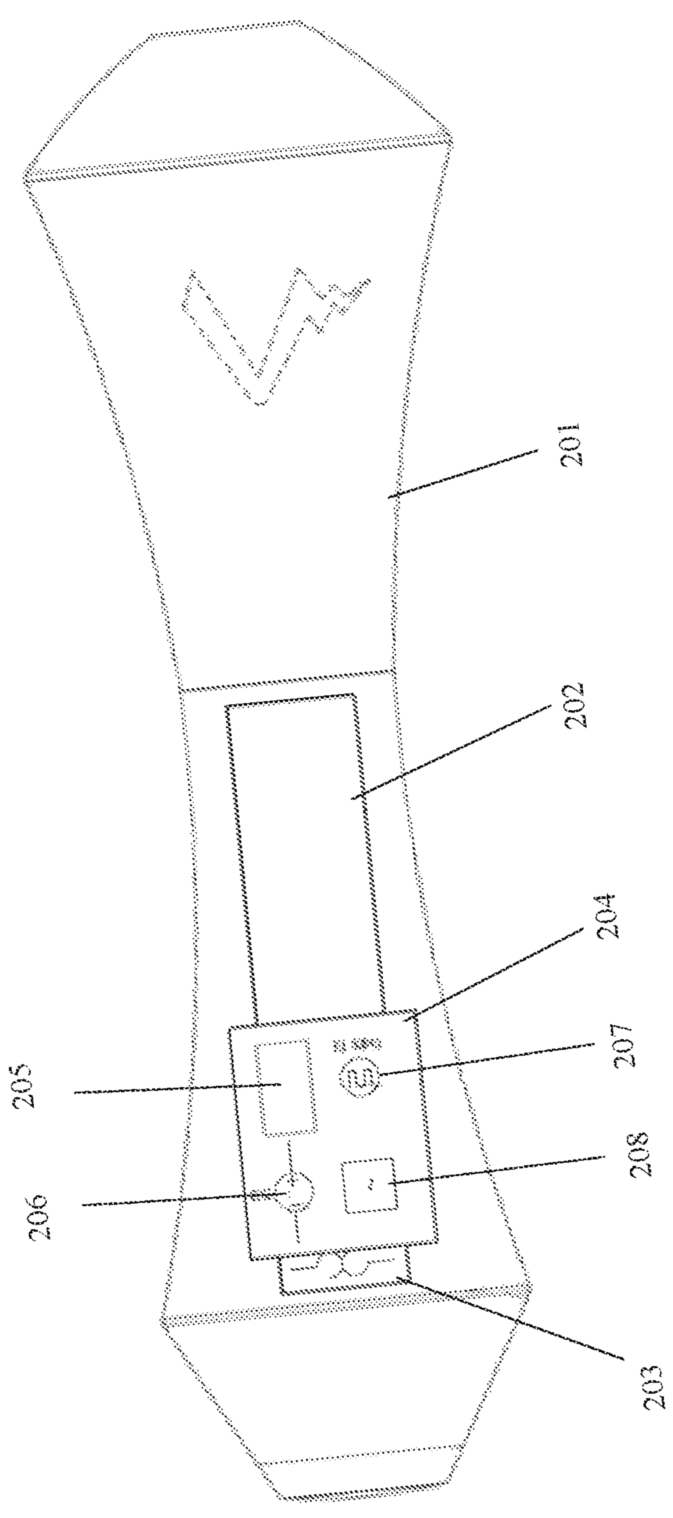
FIG. 2 is a front view of a vaporization and inhaler apparatus according to an embodiment.

FIG. 2 is a front view of a vaporization apparatus and inhaler apparatus according to an embodiment. FIG. 2 provides a partial cross-sectional view in the vaporization and inhaler apparatus 201. The vaporization and inhaler apparatus 201 includes a substance cartridge 202, containing the substance, such as a liquid formulation, for vaporization and inhaling. In example embodiments, the substance cartridge 202 may include a solid formulation that may be crushed, pulverized, or atomized, or heated and vaporized for inhalation. The substance cartridge 202 may include a substance including, but not limited to caffeine, panaxginseng, gingkobiloba, bitter orange ermge, cola-nut, guarana, natrum carbonicum, green tea, cocoa extract, cannabis, yerba mate, other vaporizable or inhalable supplements, pharmaceuticals, medicines, waxes, or liquids. The substance cartridge 202 may include a cartridge identification code. The cartridge identification code may identify the substance contained in the cartridge, flavor identification, expiration information, or other pertinent information regarding the cartridge content. The cartridge identification code may be electronically stored in a programmable memory on board the substance cartridge 202, which programmable memory may include other information such as historical usage information, including but not limited to location of use, device of use, time of use, or other data associated with the cartridge. In example embodiments, the cartridge 202 may include an RFID tag associated with the cartridge for communication with the vaporization and inhaler apparatus 201 and or one or more other devices. The RFID tag may be an active or passive tag.

The vaporization and inhaler apparatus 201 also includes a control system 204 configured to determine usage information in connection with updating and monitoring the use of substances via the vaporization and inhaler apparatus 201, for example to assist with automated refilling in accordance with various embodiments disclosed herein. The control system 204 may include a processor 205 which may be specially programmed to determine quantity of a cartridge based on usage history and parameters. For example, aerosol test may be run on substance cartridge 202. The substance cartridge may include the information in the on-board memory or the information may be pre-programmed into the processor 205. The aerosol test may be based on a fully charged battery, such as battery 206, and a filled substance cartridge, test different voltages supplied, and determine how much power vaporizes how much of the given vaporizable or dispensable product from the cartridge based on a typical vapor draw, corresponding battery power reduction in relation to the total quantity of a remaining dispensable substance. This information may be programmed into the substance cartridge 202. The aerosol test is advantageous because it permits a system that functions without additional hardware, pressure sensors, fluid monitoring, etc., that might be used in various implementations to determine the remaining dispensable substance in a device or cartridge. The aerosol test also has the advantage of permitting measuring the remaining substance without requiring the inhaler apparatus 201 to be held in a particular orientation to accurately gauge the remaining substance. This test permits the measurement to be completed with an insert in the tank in a grid like format so that a mathematical algorithm may be run to determine the remaining volume irrespective of the orientation of the inhaler apparatus 201.

The processor 205 uses this information based on the actual inhalation of the user, to accurately update and monitor the burn rate of a specific user to accurately replenish the supply for the user on time as discussed further herein. For example, the controller 204 includes a counter or timer 207 to determine a quantity such as time of vaporization or duration of inhalation. In particular embodiments, the controller 204 may monitor the duration of vaporization for example by determining the duration and quantity of heating events, by heater 203 configured to heat the substance in the substance cartridge 202 for vaporization of the substance. The controller 204 may be communicably coupled to one or more sensors 208. Sensor(s) 208 may be configured to sense a physical property such as a change in pressure to detect a draw from the vaporization and inhaler apparatus or a change in temperature or other parameter associated with a vapor draw from the vaporization and inhaler apparatus 201. One or more of the quantity and duration of a vapor draw may be analyzed by the processor 205 to determine an estimate of a value associated with a quantity of substance consumed from the substance cartridge 202. The determined quantity value may be stored by the processor, on board the controller 204 and/or on the storage of the substance cartridge 202. The determined quantity values may be aggregated by the processor 205 to estimate a consumption amount and a quantity remaining with respect to an initial quantity.

Figure 3:
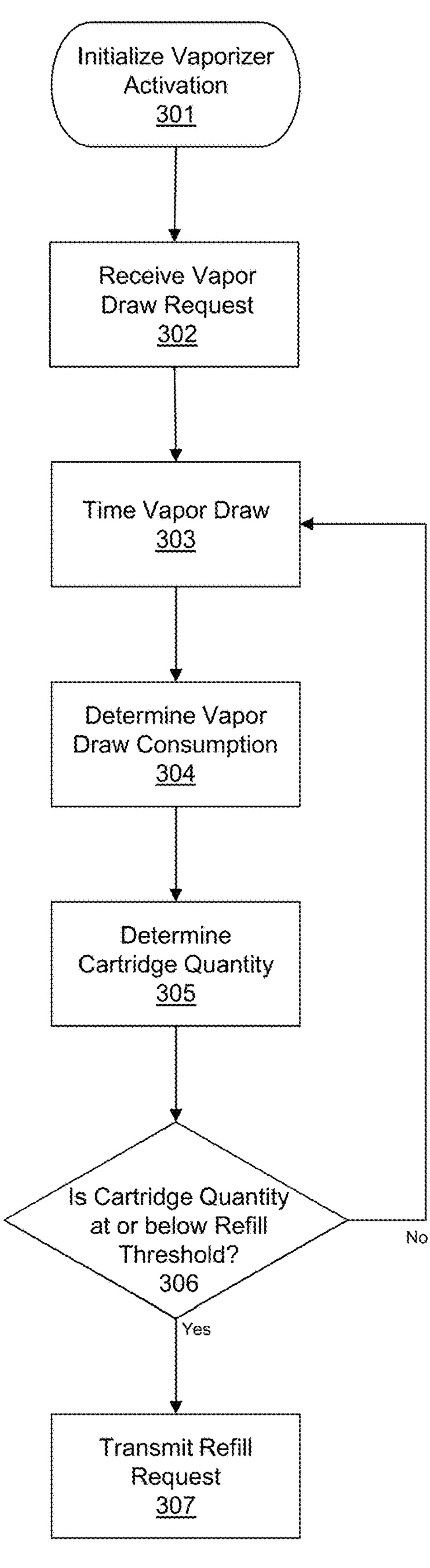
FIG. 3 is a flow diagram illustrating an operational regimen of the vaporization and inhaler apparatus of FIG. 2.

FIG. 3 is a flow diagram illustrating an operational regimen of the vaporization and inhaler apparatus of FIG. 2. At 301, the vaporization and inhaler is activated, for example in response to a user turning the device 201 on, picking the device up, requesting a vapor draw, or inserting a new or different cartridge into the device. At 302, the controller 204 of the device 201 receives a vapor draw request. The vapor draw request may include a requested duration in example embodiments. In various embodiments, the duration of the vapor draw request may be unspecified and the time of the vapor draw may be measured at 303, for example via counter 207. At 303, the duration of the vapor draw may measure a parameter such as the heating duration, which may be controlled for example by the user depressing a button to activate the heater 203 to heat the substance in the substance cartridge 202. In various embodiments, the duration of the vapor draw may measure a parameter such as a pressure change to determine the length of inhalation. At 304, the processor 204 is configured to calculate a vapor draw consumption based on one or more of the measured parameters. In example embodiments, the processor 204 may sense other parameters such as changes in pressure in the cartridge, temperature of the cartridge, changes in weight of the cartridge, or other conditions to determine the vapor draw consumption at 304. Based on the vapor draw quantity, the processor 204 determines the remaining quantity of substance in the substance cartridge 202 at 305. The 204 analyzes whether the remaining quantity of the substance in the substance cartridge 202 determined at 305 is at or below a predetermined threshold at step 306. The predetermined threshold may be manually programmed by the user or pre-programmed into the processor. The predetermined threshold may be variable based on the user location, which may be determined by a global positioning system in device 201 or other location based system and an estimated delivery time. If the quantity remaining in the substance cartridge 202 is not below the predetermined threshold, the processor 204 will continue to monitor the conditions of future draws. If the quantity remaining in the substance cartridge 202 is below a predetermined threshold, the processor 204 initiates a refill request at 307. In example embodiments, the refill request is sent via a wireless network connection to an ordering system, which may be configured to automatically send and charge the user for the refill or which may simply begin the order and send the user a notification for verification or confirmation of the request. The refill request may include the last location of the user, date and time information, substance identifying information, and user identification or device identification information.

Figure 4:
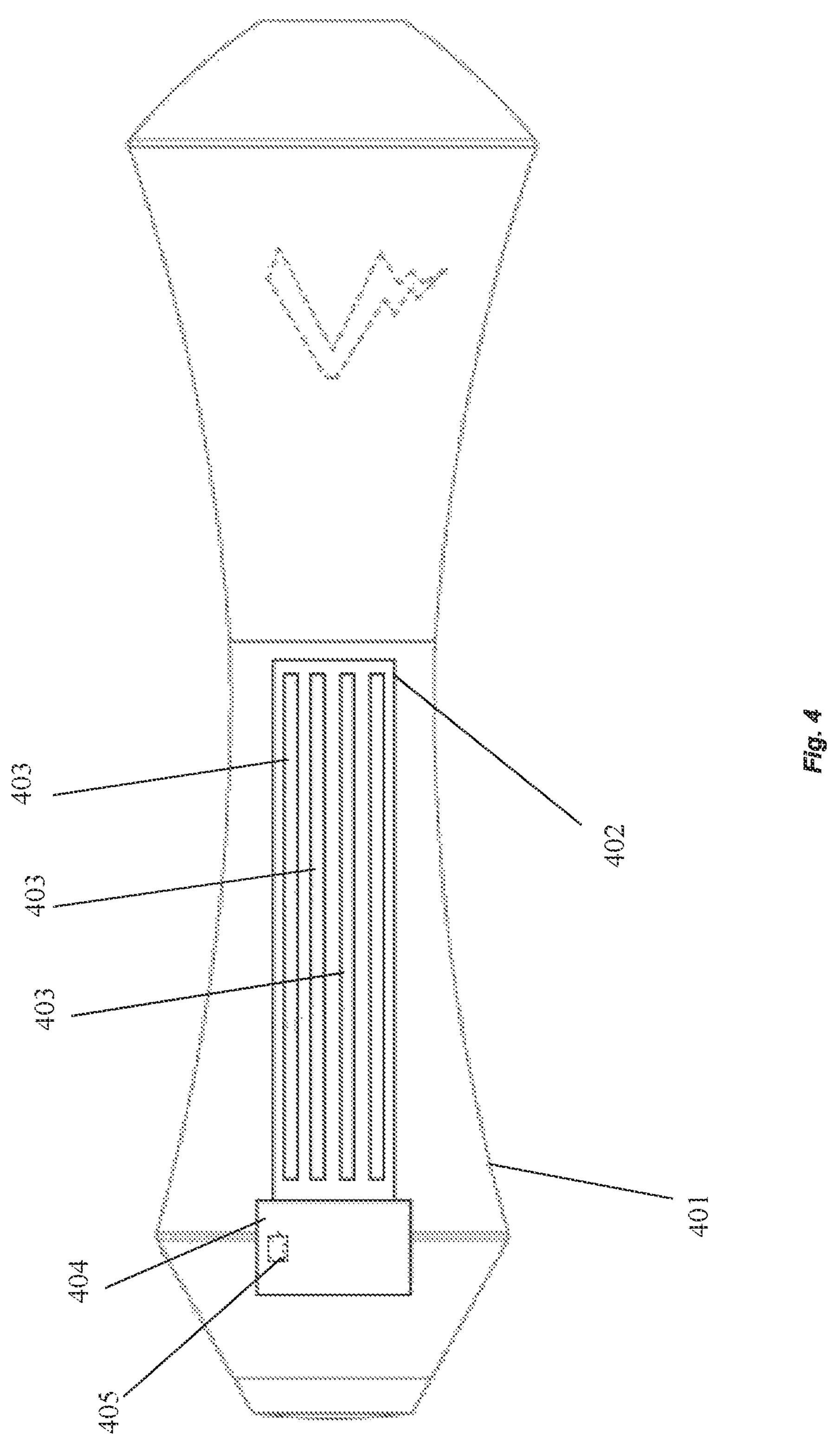
FIG. 4 is a front view of a vaporization and inhaler apparatus according to another embodiment.

FIG. 4 is a front partially cross-sectional view of a vaporization and inhaler apparatus according another embodiment. A vaporization and inhaler apparatus 401 is configured to allow inhalation of a plurality of different substance loaded into a single cartridge 402. In example embodiments, the vaporization and inhaler apparatus 401 may include vapor draw monitoring systems as discussed in connection with apparatus 201. The cartridge 402 may include a plurality of chambers or silos 403 each filled or fillable with a different substance for consumption by inhaling as disclosed herein. The cartridge 402 may be repositioned to move one or more substance silos into communication with a heater for vaporization of the content within the particular silo. In particular embodiments, the cartridge 402 may be rotatably re-positioned, for example by rotatable actuator 404 controlled by servo-controller 405. In various embodiments, the vaporization and inhaler apparatus 401 may include a single heater configured to heat only a single silo 403 of the cartridge 402 at a time. In other embodiments, the vaporization and inhaler apparatus 401 may include multiple heaters configured to heat more than one silo 403 of the cartridge 402 at a time, based on a user selection.

Repositioning the cartridge 402 for heating a particular silo 403 moves the silo 403 into communication with the heat source and with an output port of the vaporization and inhaler apparatus 401, such that when the selected substance is heated it is consumable by the user. The substance cartridge 402 may include a plurality of substances including, but not limited to caffeine, panaxginseng, gingkobiloba, bitter orange, cola-nut, guarana, natrum carbonicum, green tea, cocoa extract, cannabis, yerba mate, other vaporizable or inhalable supplements, pharmaceuticals, medicines, waxes, or liquids. The cartridge 402 may be programed with identifying information that indicates what substances are in the cartridge and what silo position the substance is positioned at accordingly. The silos 403 may each have a unique position identifier and each cartridge may have a silo quantity identifier indicating the number and/or position of each silo 403. The information may be stored in a memory device of the cartridge 402 and may be communicably retrieved or sent to the servo controller 405 to control the position of the cartridge in accordance with a user selection.

In particular embodiments, when cartridge 402 rotates, as discussed further herein, it is possible for one sub-cartridge (e.g. silo 403) to have the substance contained therein vaporized at a certain wattage/voltage, while a different sub-cartridge, for example containing a different substance, may be vaporized at a different wattage/voltage. Additionally one sub-cartridge might just dispense (and not vaporize) a substance (pill, powder, liquid, gel) or any combination of the above.

In particular embodiments each of the cartridges 402 and the silos 403, for example a cartridge containing weed, wax, or shatter, operates in a manner similar to an oven. In particular embodiments containing a liquid each of the cartridges 402 and/or the silos 403 use a wick/coil system. In particular embodiments the cartridges 402 and/or the silos 403 may use one or more of an ultrasonic diffuser, a cold air diffuser, an evaporative diffuser, or a heat diffuser. The ultrasonic diffuser uses electronic frequencies to create vibrations that are carried to the surface where oils are floating. The vibrations from the ultrasonic diffuser vaporize the oil and disperse it into the air without using any kind of heat. The cold air diffuser uses room-temperature air to blow the oil into a nebulizer where it is vaporized. The cold air diffuser can diffuse quickly and efficiently. The evaporative diffuser includes a fan that blows air through a pad or filter where the oil sits and vaporizes the oil on the pad. The heat diffuser uses a heat source to disperse the essential oil.

Figure 5:
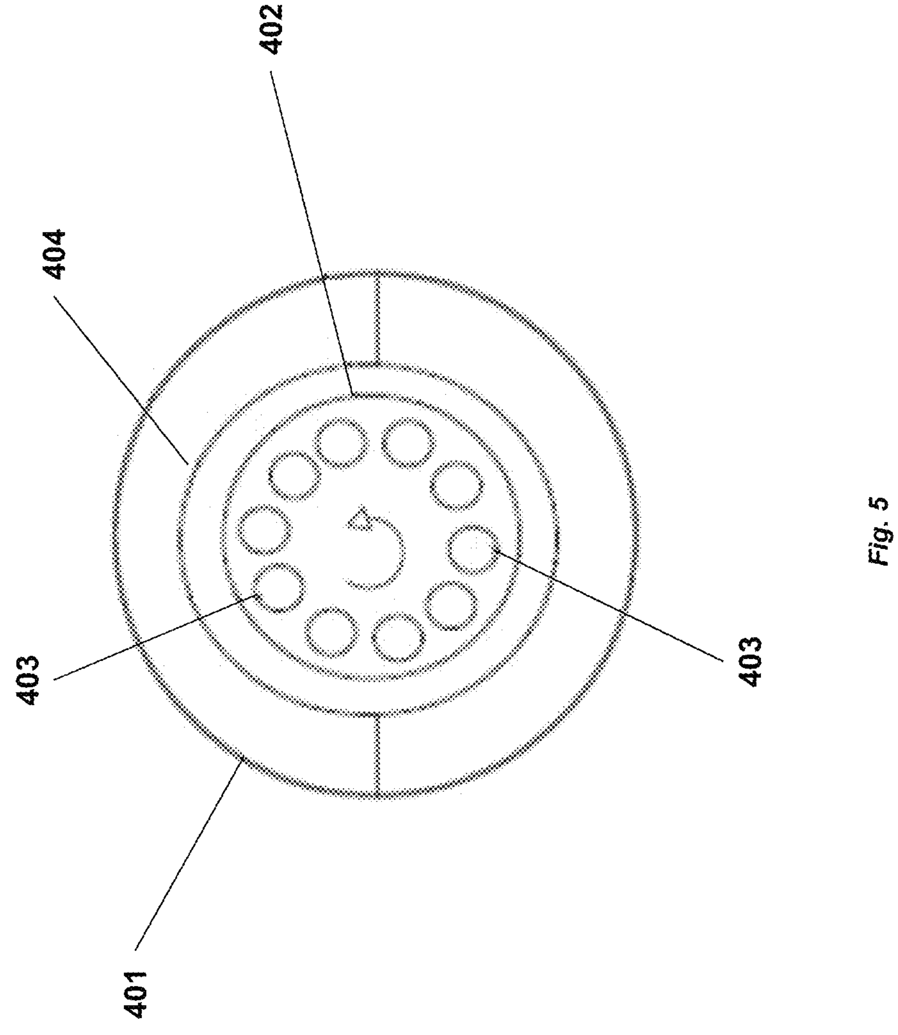
FIG. 5 is a top cross-sectional view of the vaporization and inhaler apparatus of FIG. 4.

FIG. 5 shows a top cross sectional view of the vaporization and inhaler apparatus 401. As demonstrated in FIG. 5 in accordance with various embodiments, the actuator 404 rotates the cartridge 402 to properly align the selected silo 403 containing a distinct substance for consumption by inhaling to the user preference. In example embodiments, the cartridge may remain stationary and the actuator 404 may reposition the heater for heating the silo 403 and/or may reposition an output port to release the vaporized substance. In various embodiments, the outlet port may be fixed and may be accessible to any vaporized substance of the cartridge 402. In example embodiments, repositioning of at least one of the cartridge and the vaporization heater may be achieved through linear actuation as an alternative to or in addition to rotatable actuation and repositioning.

Figure 6:
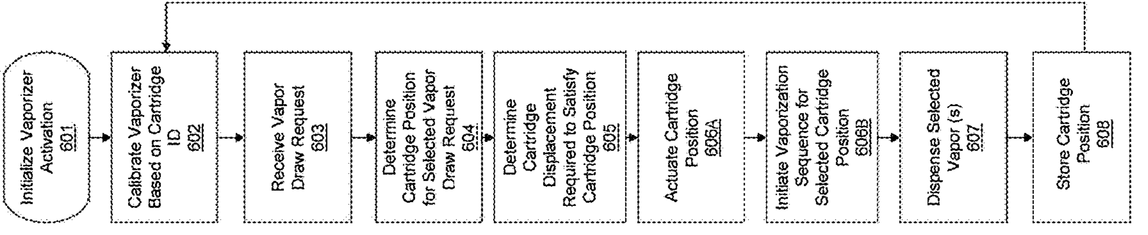
FIG. 6 is a flow diagram illustrating an operational regimen of the vaporization and inhaler apparatus of FIG. 4.

FIG. 6 is a flow diagram illustrating an operational regimen of the vaporization and inhaler apparatus of FIG. 4. At 601, the vaporization and inhaler apparatus 401 is activated, for example in response to a user turning the apparatus 401 on, picking the device up, requesting a vapor draw, or inserting a new or different cartridge 402 into the apparatus 401. At 602, the vaporization and inhaler apparatus 401 is calibrated based on the cartridge inserted in to the apparatus 401 and the information provided by the cartridge 402 regarding the device silos 403, the number of silos, the position of the silos, and the contents of the silos. At 603 the vaporization and inhaler apparatus 401 receives a vapor draw request from a user. The vapor draw request may include an indication of which one or more substance to inhale at a time. If, for example, a cartridge is loaded with two substances that should not be simultaneously mixed, the vaporization and inhaler apparatus 401 may deny the request. If the request is approved for processing, then the servo controller 405 determines the current cartridge position at 604, determines the required cartridge position for vaporization of the appropriate substance at 605, and actuates the actuator 404 at 606A to reposition the cartridge (or heater) for vaporization of the appropriate substance (s). Once the cartridge 402 is correctly positioned with respect to the heater for vaporization of the appropriate one or more substances out of the plurality of substances in the cartridge 402, vaporization is initiated at 606B and the inhalable substance is released at 607. At 608 the instant position and vaporization history associated with the vapor draw are stored so that the next vapor draw position may be appropriately determined.

In certain embodiments, the vaporization system 201 and 401 includes a vaporization control system configured to monitor consumption and/or enable variable product dispensing, for example pursuant to FIGS. 3 and 6. The vaporization control system may include a controller structured to perform certain operations to cause actuation of actuator for dispensing or to cause or prompt automated ordering of refills. The controller may be a single device or a distributed device, and the functions of the controller may be performed by hardware and/or as computer instructions on a non-transient computer readable storage medium.

C. Systems and Methods of a Vaporization and Inhaler Apparatus

The present disclosure relates to systems and methods for medical dispensing, management and monitoring. According to one aspect, a remote medical management environment can include a medical management system intermediary to a plurality of patients and a plurality of medical care providers. The medical management system can communicate with medical dispensing devices configured to dispense medication to patients. Further, the medical management system can communicate with provider devices through which medical care providers can access medicine related information of patients and provide instructions, which can administer treatment protocols to patients of the medical dispensing devices. The remote medical management environment can allow medical care providers, such as doctors, the ability to remotely manage and administer medications to patients, while at the same time, avoid medicinal drug abuse by patients.

Figure 7:
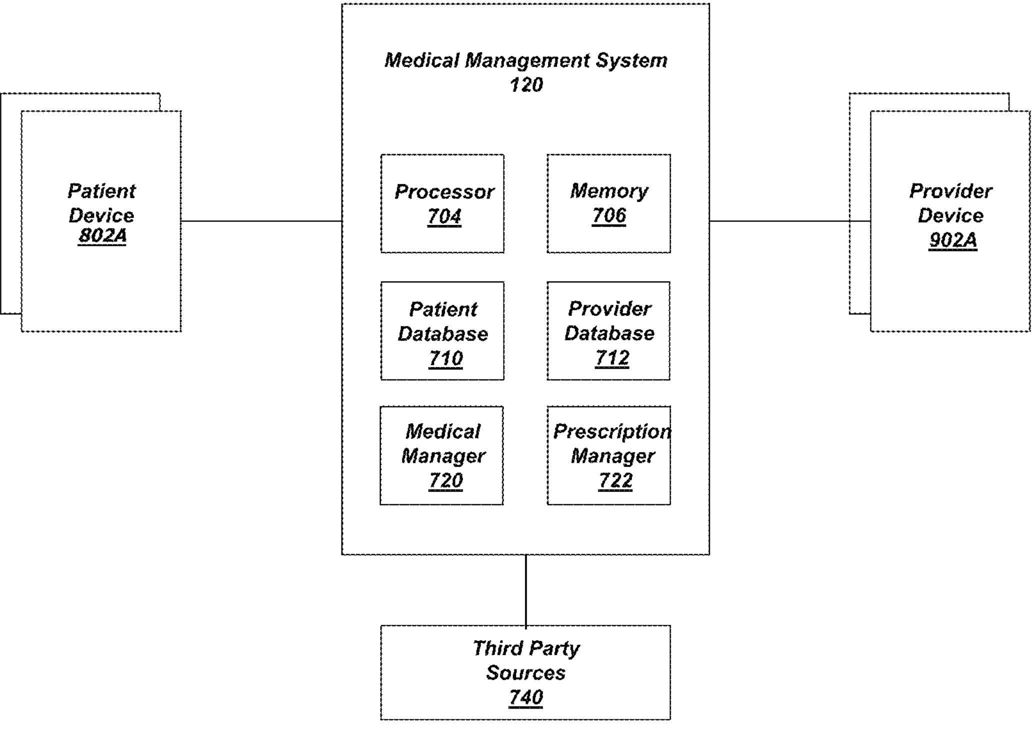
FIG. 7 is a block diagram depicting a medical management environment including a medical management system intermediary to a plurality of provider devices and patient devices.

FIG. 7 is a block diagram depicting a medical management environment including medical management system 120 intermediary to a plurality of patient devices 802A-802N and provider devices 902A-902N. The medical management system 120 can communicate with the plurality of patient devices 802 via one or more networks. Similarly, the medical management system 120 can also communicate with the plurality of provider devices 802 via one or more networks. The medical management system 120 can include one or more processors 704, memory 706, one or more patient databases 710, one or more provider databases 712, a medical manager 720 and a prescription manager 722. The medical management system 120 can also communicate with one or more third-party data sources 740, for example, weather databases, location databases, pharmaceutical drug databases, pharmacy databases, among others.

The patient database 710 can include one or more tables storing information related to one or more patients and their corresponding patient devices. The patient database can include information relating to one or more patients registered with the medical management system 120. In some implementations, the patient database can store, for each patient, one or more of the patient's name, the patient's identifier unique to the patient, the patient's date of birth, a phone number of the patient, home and work addresses of the patient, information related to the patient's medical records, for example, medical history, medical diagnosis, medical treatments, among others. In addition, the database can include prescription information for the patient, dosage information, allergies of the patient, medical care provider's name, pharmacy name, address and phone number, prescription information, health insurance information, among others. The patient database can also include a patient device identifier unique to the patient device and associated with the patient. The patient database can be maintained by the medical management system 120. In some implementations, the medical management system 120 can periodically update the patient database. In some implementations, each time the medical management system 120 receives information from a provider device 902 of a medical care provider or a patient device 802 of a patient, the medical management system 120 can identify the patient to which the information corresponds and update the patient database 710 to update an entry of the patient to include the received information.

The provider database 712 can include one or more tables storing information related to one or more medical care providers. The patient database can include information relating to one or more medical care providers registered with the medical management system 120 to manage and monitor patients and their medications via the medical management system 120. In some implementations, the provider database 712 can store, for each provider, one or more of the provider's name, the provider's identifier unique to the provider, the provider's date of birth, a phone number of the provider, home and work addresses of the provider, information related to the provider's medical licensing information, among others. In addition, the provider database 712 can include a list of patients the medical provider is authorized to treat via the medical management system 120. The provider database 712 can be maintained by the medical management system 120. In some implementations, the medical management system 120 can periodically update the provider database 712. In some implementations, each time the medical management system 120 receives information from a provider device 902 of a medical care provider or a patient device 802 of a patient, the medical management system 120 can identify the medical care provider to which the information corresponds and update the provider database 712 to update an entry of the provider to include the received information.

The medical manager 720 can include hardware, software or a combination and hardware and software. The medical manager 720 can be a script, program, file, or other software construct, which when executed by the processor 704, can be configured to communicate with one or more patient devices 802 and one or more provider devices 902. The medical manager 720 can be configured to allow a provider device 902 to remotely dispense, manage and monitor medications provided to a patient via a patient device 802.

The medical manager 720 can be configured to establish communications with the provider device 902. In some implementations, the medical manager 720 can initiate a request to communicate with the provider device 902. In some implementations, the medical manager 720 can initiate a request to communicate with the provider device 902 in response to a triggering event, for example, receiving a communication request from a patient or a patient device, determining that a patient device is running low on a prescription medication, identifying that a patient of the provider needs the provider's attention, among others. In some implementations, the medical manager 720 can receive a request from the provider device to establish a communication link with the medical manager 720. The provider may submit a request via the provider device to access a provider dashboard through which the provider can monitor the status of patients and the associated patient devices 802.

The medical manager 720 can be configured to provide a user interface to the provider device 902. In some implementations, the medical manager 720 can be configured to receive a request from the provider device 902 to access information related to a patient. The request can include identifying information of the medical care provider. The medical manager 720 can perform a lookup in the provider database 712 to validate the identity of the medical care provider and to authenticate the provider device 902 from which the request was received. The medical manager 720 can identify a patient device to which the provider 720 requests access. In some implementations, the medical manager 720 can identify the patient device from the request from the provider device 902. In some implementations, responsive to authenticating the provider device 902, the medical manager 720 can provide a dashboard on a user interface of the provider device through which the medical care provider can access information related to one or more patients of the medical care provider. In some implementations, the medical manager 720 can receive a request to access information related to a patient from the provider device. In some implementations, the medical manager 720 can identify one or more conditions that can cause the medical manager 720 to trigger a notification to the provider device of the medical care provider. The notification can be specific to a particular patient. For example, responsive to the medical manager determining that a patient device is running out of a medication, the medical manager 720 can generate a notification to the provider device of the medical care provider of the patient associated with the patient device 802 to notify the medical care provider to put in a request to refill the prescription medication.

The medical manager 720 can be configured to retrieve or receive information from the patient devices associated with patients subscribed to the medical management system 120. The medical manager 720 can identify, for each patient device 802, which medications are configured to be dispensed via the patient devices, the times at which medications are dispensed, the type and amount of medication in each channel or cartridge of the patient device, as well as other information relating to the patient device. In some implementations, the medical manager 720 can receive location information identifying a location of the patient device, a temperature within each of the medicine cartridges of the patient device, an ambient temperature around the patient device, among others.

The medical manager 720 can be configured to also receive additional information related to each of the patients. In some implementations, the medical management system 120 can communicate with other devices associated with the patient, including wearable devices that may provide physiological feedback or data to the medical management system 120. In some implementations, the wearable devices can measure body temperature, heart rate, breathing rate, oxygen volume, sugar levels, pH levels in fluids, among others.

The medical manager 720 can be configured to communicate with a patient communication device, such as a patient's smartphone or tablet, through which the medical manager 720 can be configured to send notifications to the patient reminding them to take their medications or to perform one or more tasks. In some implementations, the medical manager 720 can be configured to receive data provided by the patient via the patient communication device. In some implementations, the medical manager 720 can establish a communication link with the patient communication device, which can serve as a hub for one or more wearable devices monitoring physiological and other data of the patient as well as the patient device 802.

The medical manager 720 can be configured to actuate one or more components of the patient device 802. In some implementations, the medical manager 720 can be configured to send instructions to the patient device 802, which when executed by a processor of the patient device 802, can cause one or more valves or other actuators of the patient device 802 to dispense medications. In some implementations, the instructions can specify a length of time for which to keep the valves open to ensure that a specific amount of medication is dispensed. In some implementations, the medical manager 720 can be configured to send instructions to regulate the temperature around one or more of the cartridges within which the medications are stored. In some implementations, the medical manager 720 can send instructions to provide cooling to cartridges that include medications that need to be maintained at temperatures below the ambient temperature of the patient device 802 or provide heating to cartridges that include medications that need to be maintained at temperatures above the ambient temperature of the patient device 802.

The medical manager 720 can be configured to maintain and update records for each patient device. In some implementations the medical manager 720 can monitor and track the dispensing of medications to the patient of the patient device. The medical manager 720 can store the medication dispensing activity in one or more databases, such as the patient database. In some implementations, the medical manager 720 can monitor and track a time at which the medication was dispensed, an amount of medication dispensed, physiological and other patient related measurements around the time the medication was dispensed, a location at which the medication was dispensed, among others. In some implementations, the medical manager 720 can store this information each time medication is dispensed. In some implementations, the patient device may take over the function of monitoring and tracking medication dispensing activity and provide the information to the medical manager 720, which can then update the records of the patient device 802 in the patient database 710.

The prescription manager 722 can be configured to manage prescriptions of the patients subscribed to the medical management system 120. The prescription manager 722 can be configured to monitor the amounts of medications remaining in the patient devices such that when one or more medications are running low, the prescription manager 722 can be configured to submit requests to the medical care provider and/or one or more pharmacies to refill the prescription. In some implementations, the prescription manager 722 can be configured to automatically submit requests to pharmacies for refills. In some implementations, the prescription manager 722 can utilize health insurance information of the patient stored in the patient database 710 to submit orders for prescriptions to the pharmacies. The prescription manager 722 can be configured to identify the one or more medications included in each of the cartridges of the patient device. The prescription manager 722 can utilize one or more content sources to determine if any of the medications counteracts with one of the remaining medications in the cartridges or if they include ingredients, compounds, or medications that the patient is allergic to.

Figure 8:
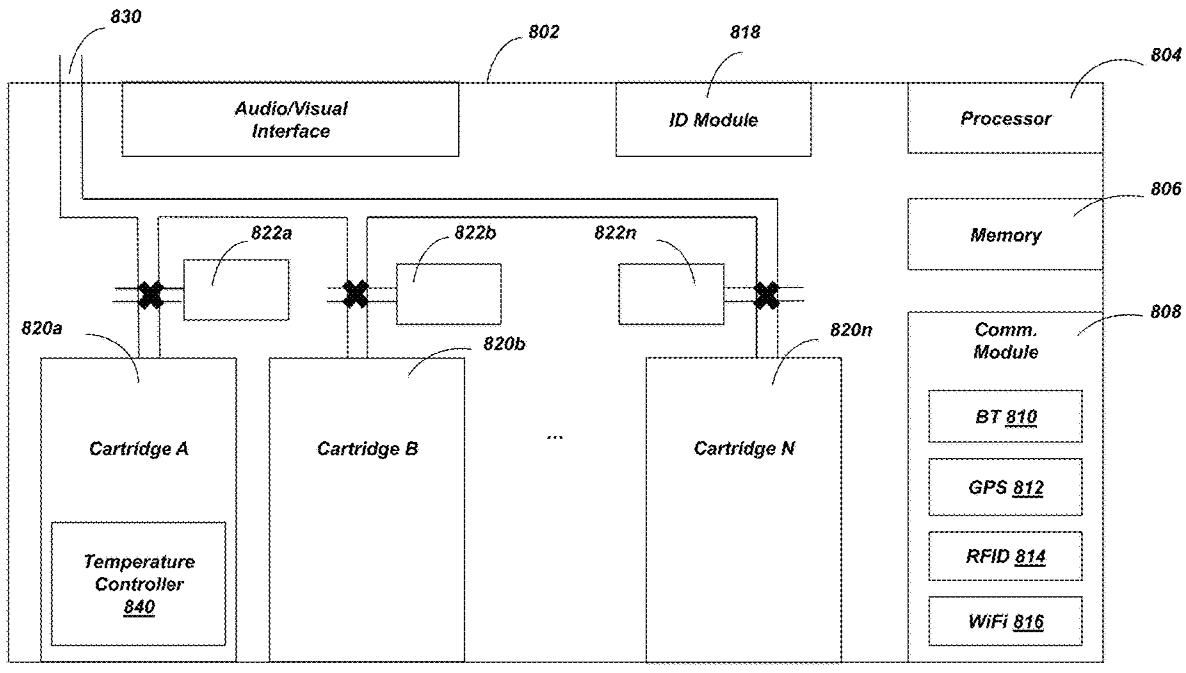
FIG. 8 is a block diagram depicting a patient device configured to dispense medication to a patient.

Referring now also to FIG. 8, FIG. 8 is a block diagram depicting a patient device configured to dispense medication to a patient. The patient device or medical dispensing device 802 includes one or more processors 804, memory 806 and at least one communication module 808. The communication module 808 can include a Bluetooth module 810, a GPS module 812, a RFID module 814 and a WiFi module 816. In some implementations, the communication module 808 can include cellular communications module that allows the medical dispensing device 802 to communicate with the medical management system 120 via cellular networks.

The medical dispensing device 802 can communicate with the medical management system 120 via one or more networks. The medical dispensing device 802 can communicate with the medical management system 120 via Bluetooth, WiFi, a wired internet connection, cellular networks, or other communication channels. In some implementations, the medical dispensing device 802 can communicate with the medical management system 120 using a patient's smartphone or other device as an intermediary. In some implementations, the medical dispensing device 802 can establish a Bluetooth connection with the patient's mobile device and the patient's mobile device can establish a connection with the medical dispensing device 802 via one or more cellular, wired or wireless internet networks. In some implementations in which the medical dispensing device 802 utilizes a Bluetooth network, the medical dispensing device 802 may operate within a communication range of a paired device, for example, a mobile phone, that is in communication with the medical management system 120.

The medical dispensing device 802 also includes an ID module 818 configured to validate communication requests received from other devices. This can serve as a security measure to prevent unauthorized devices from tampering with the medical dispensing device 802 as well as attempting to access health related information of one or more patients that subscribe to the medical management system 120. The ID module 818 can also be configured to validate the identity of the patient to which the medical dispensing device 802 is assigned. In some implementations, the ID module 818 can include a fingerprint reader or scanner to receive fingerprint information from the patient and determine if the received fingerprint information matches the patient. Similarly, the ID module 818 can include an iris scanner to validate the identity of the patient. In some implementations, the ID module 818 can include a camera for facial recognition based on one or more facial features of the patient. In some implementations, the ID module 818 can validate a patient based on voice recognition. In some implementations, the ID module 818 can validate a patient based on voice recognition. In some implementations, the ID module 818 can validate a patient via a communication link established with a trusted device, such as a smartphone or tablet. In some implementations, the patient can be required to enter a passcode or set of unique characters or gestures on a mobile device in communication with the medical dispensing device.

In some implementations, the medical dispensing device may be configured to communicate with a mobile device of the patient to verify the identity of a person accessing or requesting access to the medical dispensing device. For instance, the medical dispensing device may only dispense medication in response to receiving a communication or signal from a paired mobile device that can generate the communication or signal upon verifying the identity of the patient. In some implementations, the mobile device can verify the identity of the patient through facial recognition, fingerprint scanning, passwords, or other security measures that can be received, identified or otherwise incorporated via the mobile device. In this way, there is no need for the medical dispensing device to be designed with an integrated fingerprint scanner, camera to detect facial recognition, or keypad to receive a password from the patient, thereby reducing manufacturing costs of the medical dispensing device.

The medical dispensing device can be tamper proof. This is to prevent medication abuse and fraud. In some implementations, the medical dispensing device 820 can include an alert system that triggers an alert upon determining that the medical dispensing device has been tampered or an attempt to tamper the medical dispensing device was made. In some implementations, the medical dispensing device 820 can include one or more security modules. The security modules can include hardware and software to ensure that the medication is dispensed to an authorized user or patient. In some implementations, the medical dispensing device can include a user recognition or identification system. In some implementations, the medical dispensing device can include a fingerprint reader, an iris scanner, or any other biometric scanner to confirm the identity of the user. In some implementations, the medical dispensing device can be password protected. In some implementations the medical dispensing device can only be actuated via a second device, such as a smartphone or tablet, registered with the medical management system.

In some implementations, the location of the medical dispensing device or the mobile device with which the medical dispensing device can communicate may be monitored. In some implementations, one or more location based policies can be established to ensure additional security. For instance, the medical dispensing device may be configured to only dispense the medicine at predetermined locations, for example, a patient's home, a patient's work location, a hospital or other medical care provider's address, among others. In this way, if the device is stolen or otherwise provided to an unauthorized user, the unauthorized user may be unable to receive medication from the medical dispensing device at locations different from the predetermined locations. In addition, the medical dispensing device may only transmit or receive data from the medical management system at the predetermined locations to reduce security breaches.

The medical dispensing device 802 also includes one or more cartridges 802A-802N that contain medications to be dispensed. The cartridges can be removable from the medical dispensing device 802. In some implementations, the cartridges can be refilled. The cartridges can be shaped and sized to match an opening in the medical dispensing device and may include one or more identifying labels, tags, or other readable or detectable information that the medical dispensing device can read, identify or otherwise detect to ensure the authenticity of the cartridge. This can be used to prevent counterfeit medications or medications provided by unauthorized medical providers. In some implementations, the pharmacy providing the cartridge may include an RFID tag to the cartridge that is encrypted. In some implementations, the cartridge can be tagged in such a way that the cartridge's RFID tag can only be identified by the medical dispensing device associated with the patient for which the medication in the cartridge is prescribed. In some implementations, the cartridge can be made tamper proof such that if an unauthorized attempt to open or otherwise access or damage the cartridge is made, the medication inside the cartridge is destroyed or otherwise tainted or damaged that the medication loses any monetary value to discourage the resale of the medication or the abuse or unprescribed use of the medication. In some implementations, an acid or other compound that destroys the medication may be exposed to the medication.

The medical dispensing device can include one or more slots or channels within which the cartridges are insertable. Each slot can include a temperature controller 840 that is configured to regulate the temperature of the cartridge inserted within the slot. In some implementations, the temperature controller can include a thermoelectric cooler or a heater that can be configured to decrease or increase the temperature of the cartridge or the contents of the cartridge.

The medical dispensing device 802 can include one or more actuators **822*a*-822*n*** that are configured to actuate a switch, valve or other regulator that controls the amount of medication that is dispensed from the respective cartridge. The actuators can be configured to allow a certain amount of medication to be dispensed on a per unit time basis. In some implementations, the amount of medication dispensed per unit time may be altered based on various factors, including a size of an opening, the configuration of the actuator, and the amount of time the opening is kept open.

The actuators 332 of the medical dispensing device 802 can be configured to be remotely controlled by the medical manager 720 of the medical management system 120. In some implementations, the medical manager 720 can be configured to provide dosage instructions to the medical dispensing device 802 and the processor 804 can be configured to cause the actuators of the corresponding cartridges to be actuated in such a way that the amount of medications dispensed from the cartridges is equivalent to the desired dosage prescribed by the medical care provider. The actuators can be electronically controlled. In some implementations, the actuators can be powered via an on-board battery. In some implementations, the on-board battery can be rechargeable.

In some implementations, the medical dispensing device can operate using batteries. In some implementations, the batteries may be rechargeable or disposable. In some implementations in which the batteries are rechargeable, the batteries may be charged via a USB cable, via a power supply channel, or via wireless induction. In some implementations, to implement wireless induction, the medical dispensing device can be incorporated with a wireless charging coil, for example, a wireless charging coil supplied by DIGIKEY and manufactured by Wurth Electronics, Inc. In some implementations, the wireless charging coil can be Part Number 76080811, manufactured by Wurth Electronics, Inc. The shape, size and position of the one or more wireless charging coils can be designed to fit within the medical dispensing device.

The medical dispensing device 802 can include one or more sensors for sensing or monitoring the amount of medication dispensed from each of the cartridges. In some implementations, the sensors can monitor a weight of medication dispensed or a weight of medication remaining in the cartridge after medication is dispensed. In some implementations, the sensors can count a number of pills dispensed. In some implementations, the sensors can monitor a time for which a valve is left open and a flow rate of the medication flowing through the valve. The medical dispensing device can include sensors measuring a quantity of medication remaining in the medical dispensing device. In some implementations, the medical dispensing device can determine an amount of medication remaining in the medical dispensing device based on the amount of medication included in a medicine cartridge and an amount of medication already dispensed since the medicine cartridge was first inserted. The medical dispensing device can be configured to communicate medicine quantity levels to the medical management system 120 such that the medical management system 120 can submit orders for refills to one or more pharmacies before the medicine cartridge is completely empty.

The medical dispensing device 802, via the processor 804, can maintain a monitoring log storing information related to the monitoring of the medical dispensing device 802. The monitoring log can store information related to communications received from the medical management system 120. The log can store event related information. Examples of events include a medicine dispensing event, a medical care provider device or medical management system establishing communications with the medical dispensing device, an alarm triggering event (in the event of an attempt to tamper the medical dispensing device), location changes of the medical dispensing device, changes to ambient conditions of the medical device, for example, when the medical dispensing device senses a temperature below or above one or more predefined temperatures, detecting low medication levels in one or more cartridges of the medical dispensing device 802, among others. The activity logs can identify a date and time at which medication was dispensed, a dosage of medication dispensed as well as any other physiological measurements, for example, temperature, pulse, heart rate, blood pressure, sugar levels, among others, taken around the time the medication was dispensed. In addition to medication dispensing related activity, the activity logs can identify when a medical care provider communicated with the medical dispensing device. In some implementations, the activity logs can include information related to dosage changes as well as changes in the time at which medication is to be administered.

The medical dispensing device includes an outlet port or opening 830 through which medications within the cartridges are dispensed from the medical dispensing device. The outlet opening 830 can be configured to allow a patient to administer the medication orally. In some implementations, the opening 830 can be configured to allow medication to be dispensed in such a way that a patient can apply the medication topically, subcutaneously, pulmonary or intravenously, among others.

The patient device, otherwise referred to as a medical dispensing device can be configured to allow a medical care provider, for example, a doctor, the ability to remotely monitor, regulate and manipulate medication administration to a patient associated with the patient device. Through the medical dispensing device, the medical care provider can adjust either the dosage of medications or the time at which the medication is administered. In some implementations, the medical care provider may receive feedback through the medical dispensing device or other medical device monitoring the patient and adjust the dosage or time at which to administer medication based on the received feedback. The medical dispensing device can be equipped with a communications module that is configured to communicate with the medical management system through which the medical care provider can remotely communicate with the medical dispensing device. The communications module can include both hardware and software components that allow the medical dispensing device to receive and transmit instructions and information. In some implementations, the communications module can be configured to provide wireless communications, for example, BLUETOOTH, WiFi, cellular communications, among others. In some implementations, the communications module can be configured to communicate with another device, such as a smartphone, tablet, or other device that allows the medical dispensing device to receive and execute instructions received from the medical care provider.

In some implementations, the medical dispensing device can include a temperature control module to control the temperature of medication within the medical dispensing device. In this way, if the medicine in the medical dispensing device is to be maintained at a particular temperature, and the medical dispensing device is in a location that has an ambient temperature much higher than the temperature at which to maintain the medicine, the medical dispensing device can provide cooling to the medication. Conversely, the medical dispensing device can provide heating to medications that are supposed to be stored or maintained at temperatures higher than the ambient temperature at which the medical dispensing device is located.

In some implementations, the medical dispensing device 802 can include a thermoelectric cooler, such as one manufactured by CUSTOM THERMOELECTRIC of Bishopville, MD, USA. In some implementations, the thermoelectric cooler can be Part #08201-9G30-08RA manufactured by CUSTOM THERMOELECTRIC or other similar thermoelectric cooler. In some implementations, the medical dispensing device 802 can include one or more heat or cooling tanks that may be positioned adjacent to or around one or more cartridges of the medical dispensing device 802. In some implementations, the heating or cooling mechanism can use convection, conduction or radiation. In some implementations, a small convection system may be used to carry air from the thermoelectric cooler to a top portion of the medical dispensing device where the air will be dispersed to the atmosphere. As such, the medical dispensing device 802 may include one or more vents through which air can enter and exit the medical dispensing device.

In some implementations, the thermoelectric cooler can be part of the medical dispensing device. In some implementations, the thermoelectric cooler can be part of the cartridge that may be removable from the medical dispensing device. In some implementations in which the thermoelectric cooler is part of the cartridge, the thermoelectric cooler can be positioned within the cartridge in such a way that when the cartridge is inserted in the medical dispensing device, the thermoelectric cooler can be coupled to a power source of the medical dispensing device that can provide power to the thermoelectric cooler. In some implementations in which the thermoelectric cooler is part of the medical dispensing device, the thermoelectric cooler can be configured or positioned in such a way that the thermoelectric cooler can provide heating or cooling to the cartridge and its contents.

In some implementations, the medical dispensing device can utilize a fluid channel that includes a thermally conductive fluid, such as alcohol. The fluid channel can be positioned to extend along a side of the medical dispensing device. The fluid channel can be configured to cause heat to dissipate from around the cartridges. In some implementations, the fluid channel can be configured to provide a cooling effect similar to how laptop coolers dissipate heat generated by laptops.

In some implementations, a temperature sensor positioned within, near or adjacent to the cartridges can detect the ambient temperature around the cartridge. In some implementations, the ambient temperature may be based on weather databases based on location. In some implementations, the location of the medical dispensing device 802 can be determined from a GPS module or cellular module of the medical dispensing device 802. In some implementations, the medical dispensing device 802 can be configured or otherwise programmed to activate the cooling or heating systems of the medical dispensing device to maintain the temperature around the cartridges at temperatures suitable for storing the medications.

In some implementations, the medical dispensing device 802 can include one or more audio output components, such as a speaker, configured to emit alerts or transmit voice commands to the patient. In some implementations, the medical dispensing device 802 can communicate with a wireless or wired headphone or speaker to provide voice or audio notifications to the patient. In some implementations, the medical dispensing device 802 can include a microphone through which the patient can communicate with a medical care provider. In this way, patients that had vision or hearing impaired, may be able to locate the medical dispensing device 802 as well as receive instructions from a medical care provider remotely. In some implementations, the medical dispensing device 802 can include a screen through which a patient who has impaired hearing can receive instructions.

In some implementations, the medical dispensing device 802 can also be configured to include one or more input channels through which the medical dispensing device can receive input data from one or more wearable or portable measurement devices measuring physiological and other metrics of the patient. The data received from the measurement devices can be used by the medical dispensing device 802 to administer medication to the patient. In some implementations, the medical dispensing device 802 can utilize one or more medicine administration policies according to which dosages are administered. These policies can be established by a medical care provider of the patient and provided to the medical dispensing device 802 via the medical management system 120.

In some implementations, the medical dispensing device can be configured to report the measured data to the medical management system 120. The medical dispensing device can report the measured data periodically or upon a detected triggering event (for example, if the blood sugar level drops below a certain level, or a pulse rate or breathing rate drops below or exceeds a predefined level). The medical management system 120 can be configured to identify triggering events based on the data received and may initiate a communication with the medical care provider alerting the provider of a medical condition.

The medical care provider, via the provider device 902, can send instructions to the medical dispensing device to administer medication to the patient. In some implementations, the provider device 902 can modify a dosage regimen programmed for the medical dispensing device by sending instructions to the medical dispensing device 802 via the medical management system 120.

Figure 9:
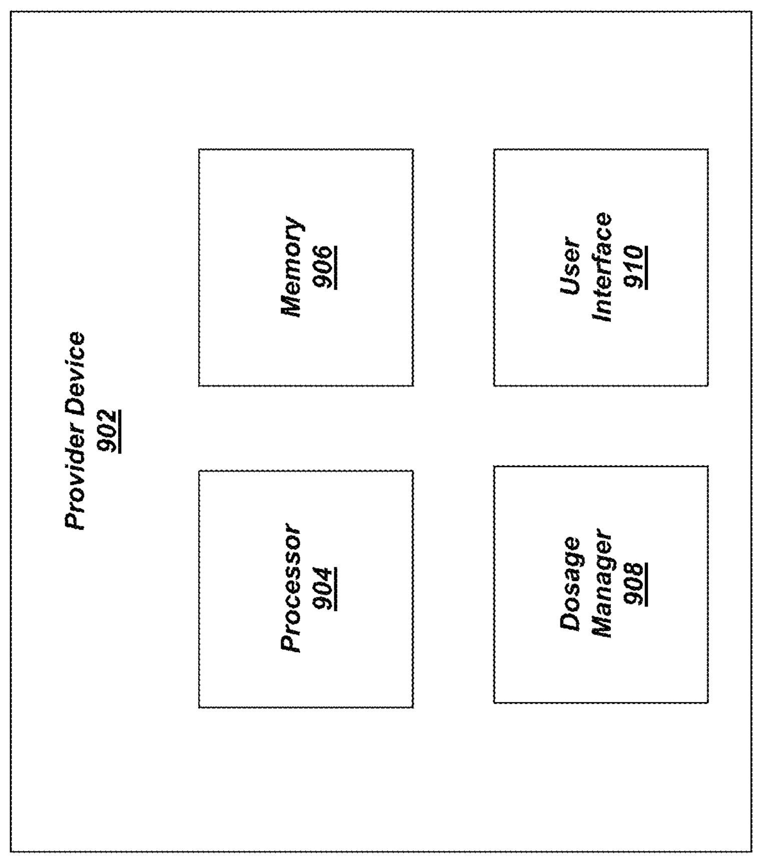
FIG. 9 is a block diagram depicting a provider device configured to allow a medical care provider to manage medications of patients receiving medication through the patient device of FIG. 8.

FIG. 9 is a block diagram depicting a provider device configured to allow a medical care provider to manage medications of patients receiving medication through the patient device of FIG. 8. The provider device 902 can include a processor 904, a memory 906, a dosage manager 908 and a user interface 910.

The dosage manager 908 can be configured to manage, administer and monitor dosage information provided to each of the medical dispensing devices 802 of patients of the medical care provider of the provider device 902. The dosage manager 908 can include hardware, software or a combination of both to communicate with each of the medical dispensing devices 802 via the medical management system 120. The dosage manager 908 can receive instructions from the medical care provider via the user interface 910, which can be provided for display on a display of the provider device 902. The provider can view patient related data on the user interface, including but not limited to current dosage levels of medications, the identity of medications loaded in the cartridges of the medical dispensing device 802, as well as data from one or more monitoring devices monitoring patient's vitals, physiological metrics, among others. The provider can send instructions to administer, modify or otherwise alter dosages to the medical dispensing devices 802. The dosage manager 908 can receive these instructions and provide instructions to the medical management system 120 such that the correct dosage can be administered at the medical dispensing device 802.

While the invention has been particularly shown and described with reference to specific embodiments, it should be understood by those skilled in the art that various changes in form and detail may be made therein without departing from the spirit and scope of the invention described in this disclosure.

While this specification contains many specific embodiment details, these should not be construed as limitations on the scope of any inventions or of what may be claimed, but rather as descriptions of features specific to particular embodiments of particular inventions. Certain features described in this specification in the context of separate embodiments can also be implemented in combination in a single embodiment. Conversely, various features described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated in a single software product or packaged into multiple software products.

References to "or" may be construed as inclusive so that any terms described using "or" may indicate any of a single, more than one, and all of the described terms.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain embodiments, multitasking and parallel processing may be advantageous.

In certain embodiments, the controller includes one or more modules structured to functionally execute the operations of the controller. In certain embodiments, the controller includes sensor modules configured to measure time lapse, energy consumption, product consumption, rotation position, a change in rotation, linear position, a change in a linear position, product location, product ingredients, or other vaporization system operating parameters or conditions impacting the use, dispensing, or operation of the vaporization system.

The description herein including modules emphasizes the structural independence of the aspects of the controller, and illustrates one grouping of operations and responsibilities of the controller. Other groupings that execute similar overall operations are understood within the scope of the present application. Modules may be implemented in hardware and/or as computer instructions on a non-transient computer readable storage medium, and modules may be distributed across various hardware or computer based components.

Example and non-limiting module implementation elements include sensors providing any value determined herein, sensors providing any value that is a precursor to a value determined herein, datalink and/or network hardware including communication chips, oscillating crystals, communication links, cables, twisted pair wiring, coaxial wiring, shielded wiring, transmitters, receivers, and/or transceivers, logic circuits, hard-wired logic circuits, reconfigurable logic circuits in a particular non-transient state configured according to the module specification, any actuator including at least an electrical, hydraulic, or pneumatic actuator, a solenoid, an op-amp, analog control elements (springs, filters, integrators, adders, dividers, gain elements), and/or digital control elements.

Non-limiting examples of various embodiments are disclosed herein. Features from one embodiments disclosed herein may be combined with features of another embodiment disclosed herein as someone of ordinary skill in the art would understand.

As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of apparatuses or the components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

While various inventive embodiments have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive embodiments described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way unless otherwise specifically noted. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one." As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed:

1. An apparatus comprising:

one or more cartridges comprising a plurality of chambers, each chamber configured to store one or more substances to dispense to a user;

one or more rotatable actuators configured to reposition the one or more cartridges for dispensing of the one or more substances from the plurality of chambers;

a plurality of heating elements configured to heat the one or more substances of the plurality of chambers to a point of vaporization to generate a vaporized form of the one or more substances, each of the plurality of heating elements positioned in thermal communication with a respective one of the plurality of chambers and configured to be selectively energized, such that at least two of the plurality of heating elements are energizable at a time based on a user selection;

an outlet port through which the vaporized form of the one or more substances is inhalable by the user;

a communications module configured to communicate via a wireless transmitter to one or more networks with a system; and one or more processors configured to:

restrict dispensing the one or more substances to one or more predetermined locations;

identify that the apparatus is at or within a predetermined distance of the one or more predetermined locations;

receive from the system over the one or more networks, via the communications module, at the one or more predetermined locations of the user, instructions on a dosage and timing of administering the dosage for dispensing the one or more substances to the user; and causing, via the one or more rotatable actuators, the apparatus to dispense the one or more substances from the plurality of chambers based on the user selection, and causing at least two of the plurality of heating elements to heat the one or more substances into the vaporized form in accordance with the user selection and the dosage and time of administering the dosage.

2. The apparatus of claim 1, wherein the one or more substances comprises cannabis.

3. The apparatus of claim 1, wherein the one or more processors are configured to determine a remaining quantity of the one or more substances of the one or more cartridges and to monitor a consumption rate of the one or more substances via vaporization.

4. The apparatus of claim 1, wherein the one or more processors are configured to communicate one of a quantity or a consumption rate to the system via the communications module.

5. The apparatus of claim 1, wherein the apparatus is further configured to position, via the one or more rotatable actuators, a selected one of the plurality of chambers at a heating location associated with a respective heating element of the plurality of heating elements such that the selected chamber is in communication with the respective heating element for vaporization.

6. The apparatus of claim 1, further comprising a security module to authorize the user and ensure that the dosage is administered to the authorized user.

7. The apparatus of claim 1, wherein the one or more processors are further configured to cause the one or more rotatable actuators to actuate the one or more cartridges to dispense an amount of the one or more substances corresponding to the dosage.

8. The apparatus of claim 1, further comprising a temperature control module to control a temperature of heating the one or more substances.

9. The apparatus of claim 1, wherein the instructions from the system provides temperature information wherein the one or more processors are further configured to cause the plurality of heating elements to heat the one or more substances according to the temperature information.

10. A system, comprising:

a management system to communicate with a plurality of dispensing devices that dispense one or more substances to a plurality of users;

a dispensing device of the plurality of dispensing devices comprising:

a communications module to communicate via one or more networks with the management system;

one or more cartridges comprising a plurality of chambers, each chamber configured to store the one or more substances;

one or more rotatable actuators configured to reposition the one or more cartridges for dispensing of the one or more substances from the plurality of chambers;

a plurality of heating elements configured to heat the one or more substances of the plurality of chambers to a point of vaporization to generate a vaporized form of the one or more substances, each of the plurality of heating elements positioned in thermal communication with a respective one of the plurality of chambers and configured to be selectively energized, such that at least two of the plurality of heating elements are energizable at a time based on a user selection of a user of the plurality of users;

an outlet port through which the vaporized form of the one or more substances is inhalable by the user; and one or more processors configured to receive instructions on a dosage from the management system and restrict dispensing the one or more substances to one or more predetermined locations;

wherein the management system communicates remotely via the one or more networks, and responsive to input from the user of the management system, the one or more processors configured to receive instructions to administer the dosage to the user of the management system, wherein the dispensing device receives the instructions on the dosage and timing of the dosage from the management system at the one or more predetermined locations; and wherein the one or more processors, responsive to receiving the instructions;

identify that the dispensing device is at or within a predetermined distance of the one or more predetermined locations; and cause, via the one or more rotatable actuators, the dispensing device to dispense the one or more substances from the plurality of chambers based on the user selection, and causing at least two of the plurality of heating elements to heat the one or more substances into the vaporized form in accordance with the user selection and the dosage and timing of the dosage.

11. The system of claim 10, wherein the dispensing device further comprises a security module to authorize the user and ensure that the dosage is administered to the authorized user.

12. The system of claim 11, wherein the management system is configured to receive feedback from the dispensing device on use of the dispensing device.

13. The system of claim 11, wherein the security module comprises one or more of the following: a fingerprint reader, an iris scanner, a biometric scanner, a camera, a voice recognition system, or a communication link with a trusted mobile device.

14. The system of claim 11, wherein the dispensing device is configured to maintain activity logs to identify one or more of the following: a date and time the one or more substances are dispensed and a dosage of the one or more substances dispensed.

15. The system of claim 11, wherein the one or more substances comprises one or more of the following: cannabis, caffeine, panax ginseng, gingko biloba, bitter orange, cola-nut, guarana, natrum carbonicum, green tea, cocoa extract, and yerba mate.

16. The system of claim 11, wherein the one or more processors are configured to determine a remaining quantity of the one or more substances of the one or more cartridges and to monitor a consumption rate of the one or more substances via vaporization.

17. The system of claim 16, wherein the one or more processors are configured to communicate one of the remaining quantity or the consumption rate to the system via the communications module.

18. The system of claim 10, wherein the one or more processors are further configured to cause the one or more rotatable actuators to actuate the one or more cartridges to dispense an amount of the one or more substances corresponding to the dosage.

19. The system of claim 10, wherein the dispensing device is further configured to position, via the one or more rotatable actuators, a selected one of the plurality of chambers at a heating location associated with a respective heating element of the plurality of heating elements such that the selected chamber is in communication with the respective heating element for vaporization.

* * * * *